United States Patent
Jenssens et al.

(10) Patent No.: US 8,138,334 B2
(45) Date of Patent: Mar. 20, 2012

(54) SUBSTITUTED OXA-DIAZA-SPIRO-[5.5]-UNDECANONE DERIVATIVES AND THEIR USE AS NEUROKININ ANTAGONISTS

(75) Inventors: Frans Eduard Jenssens, Bonheide (BE); Sophie Coupa, Louviers (FR); Alain Philippe Poncelet, Le Manoir sur Seine (FR); Bruno Schoentjes, Bois-Guillaume (FR)

(73) Assignee: Janssen Pharmaceutica N.V. (BE)

( * ) Notice: Subject to any disclaimer, the term of this patent is extended or adjusted under 35 U.S.C. 154(b) by 820 days.

(21) Appl. No.: 11/913,890

(22) PCT Filed: Mar. 3, 2006

(86) PCT No.: PCT/EP2006/060419
§ 371 (c)(1),
(2), (4) Date: Nov. 8, 2007

(87) PCT Pub. No.: WO2006/094934
PCT Pub. Date: Sep. 14, 2006

(65) Prior Publication Data
US 2010/0292228 A1    Nov. 18, 2010

Related U.S. Application Data

(63) Continuation of application No. 11/264,680, filed on Nov. 1, 2005, now Pat. No. 7,731,648.

(60) Provisional application No. 60/732,368, filed on Nov. 1, 2005.

(30) Foreign Application Priority Data

Mar. 3, 2005    (EP) ..................... 05101657

(51) Int. Cl.
*C07D 285/16* (2006.01)
*C07D 407/00* (2006.01)
*C07D 493/00* (2006.01)
*A01N 43/42* (2006.01)
*A61K 31/44* (2006.01)
(52) U.S. Cl. ................ 544/71; 514/278; 549/265
(58) Field of Classification Search ............. 544/71; 549/265; 514/278
See application file for complete search history.

(56) References Cited

U.S. PATENT DOCUMENTS

| 5,403,593 | A | 4/1995 | Royce | |
| 7,332,500 | B2* | 2/2008 | Gabriel et al. | 514/277 |
| 2005/0176703 | A1* | 8/2005 | Gabriel et al. | 514/230.5 |

FOREIGN PATENT DOCUMENTS

| EP | 1308439 B2 | 5/2003 |
| WO | WO 9219227 A2 | 11/1992 |
| WO | WO 9724324 A1 | 7/1997 |
| WO | WO 9724350 A1 | 7/1997 |
| WO | WO 9724356 A1 | 7/1997 |
| WO | WO 9911261 A1 | 3/1999 |
| WO | WO 0194346 A1 | 12/2001 |
| WO | WO 02/092604 | 11/2002 |
| WO | WO 03057698 A2 | 7/2003 |

OTHER PUBLICATIONS

Aguiar, et al., "Effects of microinjections of the neuropeptide substance P in the dorsal periaqueductal gray on the behaviour of rats in the plus-maze test", *Physiol. Behav.* 60:1183-1186 (1996).
Ballard et al., "Inhibition of shock-induced foot tapping behaviour in the gerbil by a tachykinin $NK_1$ receptor antagonist", *Eur. J. Pharmacology*, 412:255-264 (2001).
Betrand et al., "Tachykinin and kinin receptor antagonists: therapeutic perspectives in allergic airway disease" *Trends Pharmacol. Sci* 17: 255-259 (1996).
Brodin et al., "Effects of sequential removal of rats from a group cage, and of individual housing of rates, on substance P, cholecystokinin and somatostatin levels in the periaqueductal grey and limbic regions", Neuropeptides 26: 253-260 (1994).
Campos et al., "Prevention of cisplatin-induced emeis by the oral neurokinin-1 antagonist, MK-869, in combination with granisetron and dexamethasone or with dexamethasone alone" *J. Clin. Oncol.*, 19: 1759-1767 (2001).

(Continued)

*Primary Examiner* — Sreeni Padmanabhan
*Assistant Examiner* — Kendra D Carter
(74) *Attorney, Agent, or Firm* — Kiera K. Mathey

(57) ABSTRACT

This invention concerns substituted oxa-diaza-spiro-[5.5]-undecanone derivatives having neurokinin antagonistic activity, in particular an $NK_1$ antagonistic activity, an $NK_3$ antagonistic activity, a combined $NK_1/NK_2$ antagonistic activity and a combined $NK_1/NK_2/NK_3$ antagonistic activity, their preparation, compositions comprising them and their use as a medicine, in particular for the treatment and/or prophylaxis of schizophrenia, emesis, anxiety and depression, irritable bowel syndrome (IBS), circadian rhythm disturbances, preeclampsia, nociception, pain, in particular visceral and neuropathic pain, pancreatitis, neurogenic inflammation, asthma, chronic obstructive pulmonary disease (COPD) and micturition disorders such as urinary incontinence. The compounds according to the invention can be represented by general Formula (I) and comprises also the pharmaceutically acceptable acid or base addition salts thereof, the stereochemically isomeric forms thereof, the N-oxide form thereof and prodrugs thereof, wherein all substituents are defined as in Claim 1.

(I)

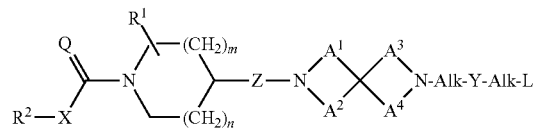

22 Claims, 5 Drawing Sheets

OTHER PUBLICATIONS

Figure 1:
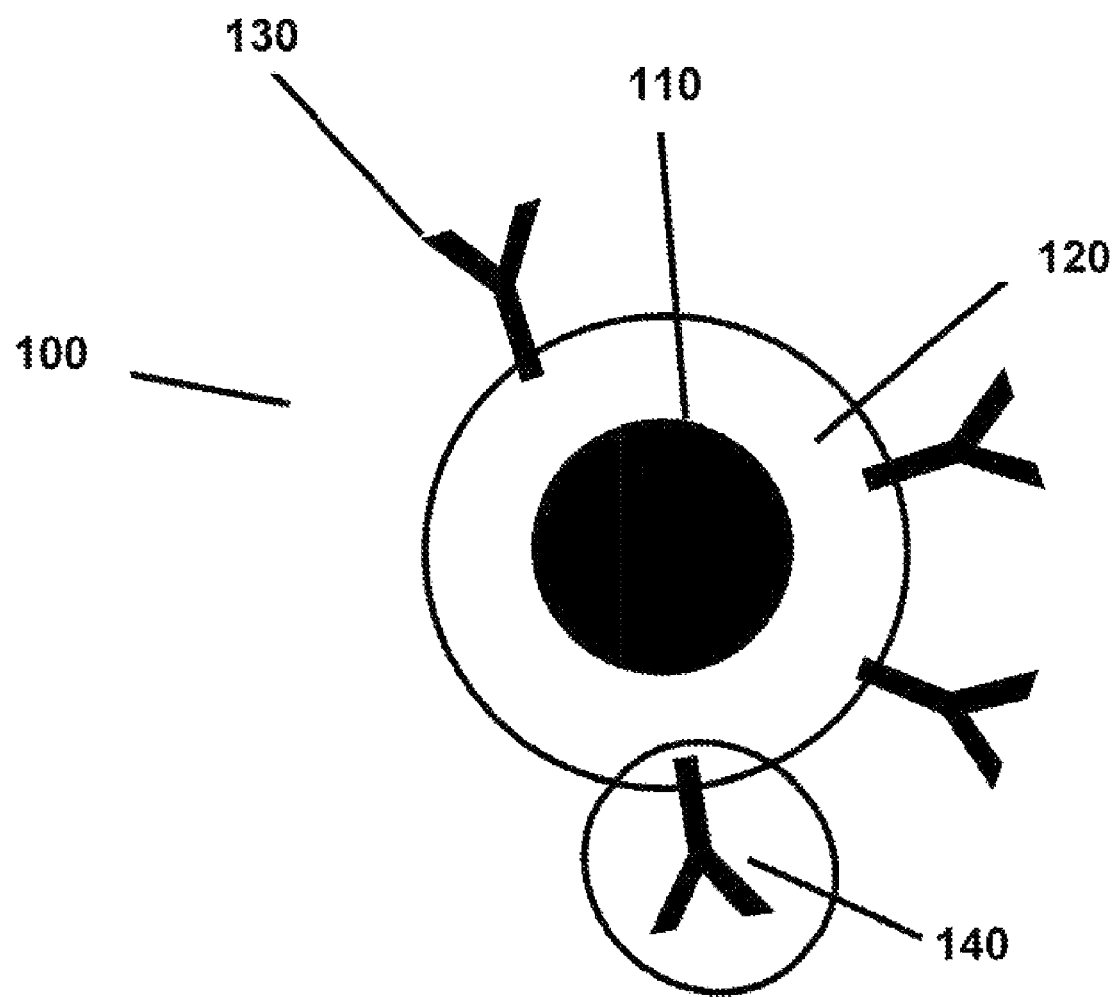
Figure 2:
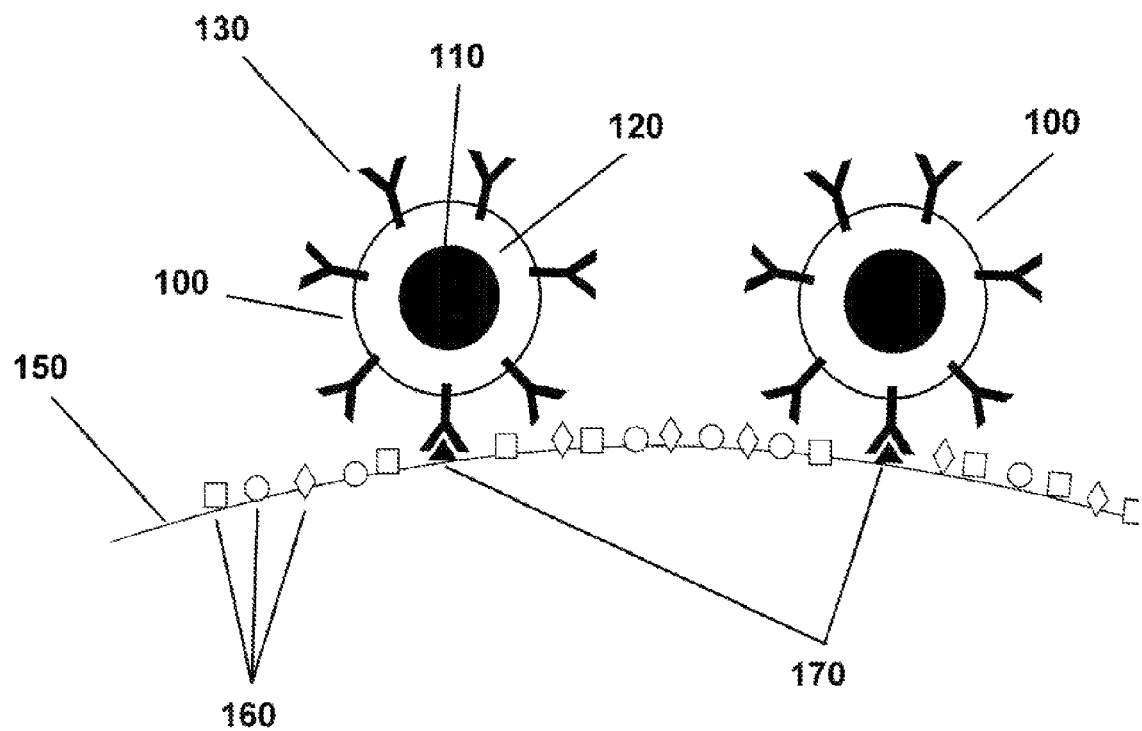
Figure 3:
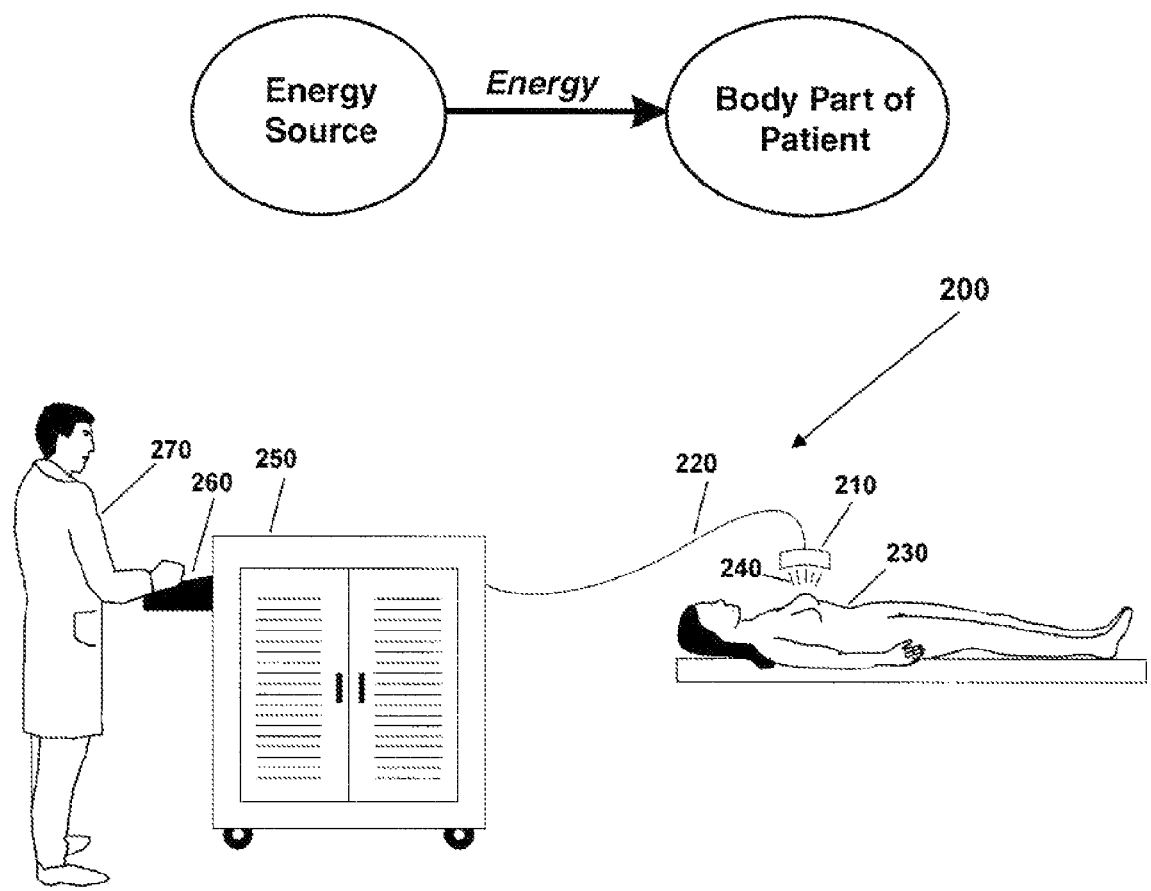
Figure 4:
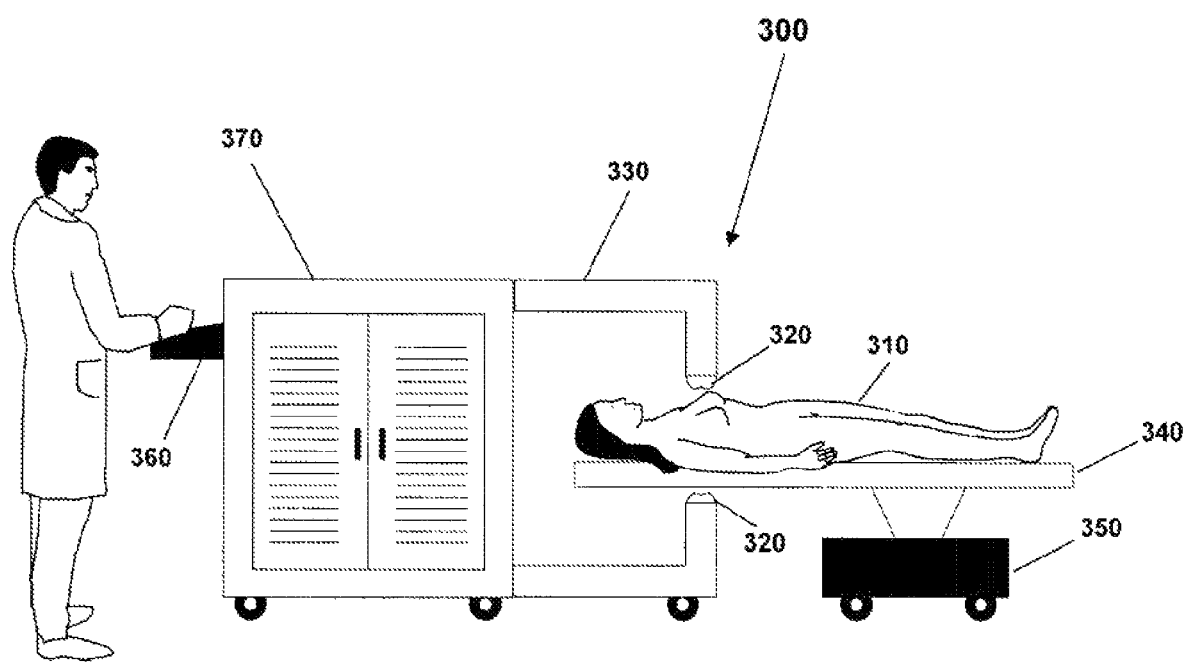
Figure 5:
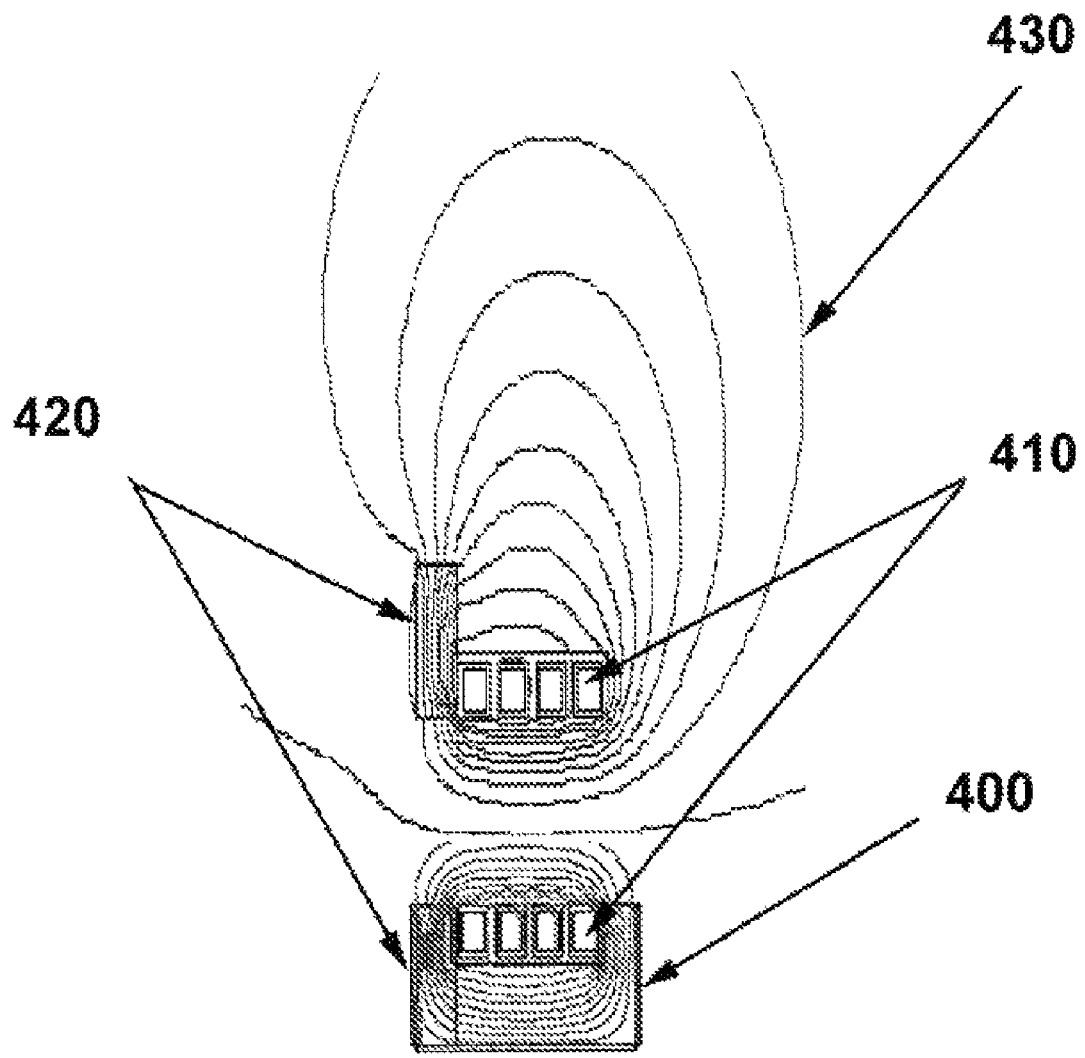

Cocquyt et al., "Comparison of L-758, 298, a prodrug for the selective neurokinin-1 antagonist, L-754,030, with ondansetron for the prevention of cisplatin-induced emesis", *Eur. J. of Cancer* 37: 835-842 (2001).

Culman et al., "Central tachykinins: mediators of defence reaction and stress reactions[1]", Can. J. Physiol. Pharmacol., 73: 885-891 (1995).

De Mulder, et al., "Ondansetron compared with high-dose metoclopramide in prophylaxis of acute and delayed cisplatin-induced nausea and vomiting", *Annuals of Internal Medicine* 113:834-840 (1990).

Elliot, P.J., "Place aversion induced by the substance P analogue, dimethyl-C7, is not state dependent: implication of substance P in aversion", *Exp. Brain. Res.* 73: 354-356 (1988).

Gaudreau et al., "Role of tachykinin $NK_1$, $NK_2$ and $NK_3$ receptors in the modulation of visceral hypersensitivity in the rat", *Neuroscience Letters*, 351:59-62 (2003).

Giardina et al., "Recent advances in neurokinin-3 receptor antagonists", Exp. Opin. Ther. Patents, 10(6):939-960 (2000).

Goldstein et al., "Study of the analgesic effect of lanepitant in patients with osteoarthritis pain" *Clin. Pharm. Ther.* 67:419-426 (2000).

Hesketh et al., "Proposal for classifying the acute emetogenicity of cancer chemotherapy", *J. Clin. Oncol.* 15:1, 103-109 (1997).

Hesketh et al., "Randomized phase II study of the neurokinin 1 receptor antagonist CJ-11,974 in the control of cisplatin-induced emesis", *J. Clin. Oncol.* 17:338-343 (1999).

Julia et al., "Role of neurokinin 3 receptors on rsponses to colorectal distention in the rat: electrophysiological and behavioral studies", *Gastroenterology*, 116:1124-1131 (1999).

Kamp et al., "Combinations of neurokinin receptor antagonists reduce visceral hyperalgesia", *J. Pharmacol. Exp. Ther*. 299:105-113 (2001).

Kochhar et al. "The effects of slugging and recompression on pharmaceutical excipients", International Journal of Pharmaceutics, 155: 35-43 (1995).

Kramer et al., "Distinct mechanism for antidepressant activity by blockade of central substance P receptors", *Science* 281:1640-1645 (1998).

Krase et al., "Substance P is involved in the sensitization of the acoustic startle response by footshocks in rats", Behav. Brain Res. 63: 81-88 (1994).

Kris et al., "Incidence, course, and severity of delayed nausea and vomiting following the administration of high-does cisplatin", *J. Clin. Oncol.* 3:10, 1379-1384 (1985).

Le Jeune, et al., "Selective, non-peptidergic neurokinin$_1$ ($NK_1$) antagonists enhance the activity of frontocortical dopaminergic and adrenergic, but not serotonergic, pathways in rats", Soc. Neurosci, Nov. 2001.

Lieberman et al. "Size reduction passage", Pharmaceutical Dosage Forms, 145-157 (1989).

Longmore, J. et al., "Neurokinin receptors", DN&P 8(1): 5-23 (1995).

Lundberg, J.M., "Tachykins, sensory nerves, and asthma—an overview[1]"Can. J. Physiol. Pharmacol. 73: 908-914 (1995).

Maggi et al, "The mammalian tachykinin receptors", *Gen. Pharmacol.*, 26:5, 911-944 (1995).

Maggi et al., "The dual nature of the tachykinin NK1 receptor", *Trends Pharmacol. Sci.* 18:351-355 (1997).

Mattson et al., "An improved method for reductive alkylation of amines using titanium (IV) isopropoxide and sodium cyanoborohydride", *J. Org. Chem.* 55:8 2552-2554 (1990).

Megens et al., "Pharmacological profile of )2R-trans)4-[1-[3,5-bis (trifluoromethyl)benzoyl]-2-29phenylmethyl]-4-piperidinyl]-N-(2,6-dimethlphenyl)-1-acetamide (S)-hydroxybutanedioate (R116301), an orally and centrally active neurokinin-1 receptor antagonist", *J. Pharmacol. Exp. Ther.* 302:2 696-709 (2002).

Navari et al., "Reduction of cisplatin-induced emesis by a selective neurokini-1-receptor antagonist" *N. Engl. J. Med.* 340:3 190-195 (1999).

Naylor, et al., "Emesis and anti-emesis", *Cancer. Surv.* 21:117-135 (1996).

Okano et al., "Effects of TAK-637, a novel neurokinin-1 receptor antagonist, on colonic function in vivo", *J. Pharmacol. Exp. Ther.* 298:559-564 (2001).

Parrott, E.L., "Densification of powders by concavo-convex roller compactor", Journal of Pharmaceutical Sciences, 70:3, 288-291 (1980).

Piedimonte, et al., "A new NK1 receptor antagonist (CP-99,994) prevents the increase in tracheal vascular permeability produced by hypertonic saline", *J. Pharmacol. Exp. Ther.*, 266: 270-273 (1993).

Regoli et al., "Receptors and antagonists for substance P and related peptides", *Pharmacol. Rev*, 46(4) 551-599 (1994).

Rein et al., "New treatment strategies in schizophrenia" ACNP Meeting, Dec. 2001, 1 page.

Rocksloh et al. "Optimization of crushing strength and disintegration time of a high-dose plant extract tablet by neural networks", Drug Development and Industrial Pharmacy, 25(9): 1015-1025 (1999).

Roila et al., "Prevention of chemotherapy- and radiotherapy-induced emesis: results of the perugia consensus conference", Annals Oncol. 9:811-819 (1998).

Roila, F., "Ondansetron plus dexamethasone compared to the 'standard' metoclopramide combination", *Oncology* 50: 163-167 (1993).

Rudd, et al. "The action of the $NK_1$ tachykinin receptor antagonist, CP 99,994, in antagonizing the acute and delayed emesis produced by cisplatin in the ferret", *Br. J. Pharmacol.* 119: 931-936 (1996).

Rudd, et al., "Effects of 5-$HT_3$ receptor antagonists on models of acute and delayed emesis induced by cisplatin in the ferret", *Neuropharmacology* 33:12, 1607-1608 (1994).

Rupniak et al., "Discovery of the anti-depressant and anti-emetic efficacy of substance P receptor ($NK_1$) antagonists", *Trends Pharmacol. Sci.* 20:485-490 (1999).

Sam et al., "Action of glucocorticoids to antagonise cisplatin-induced acute and delayed emesis in the ferret", *Eur J. Pharmacol.*, 417:231-237 (2001).

Shirayama et al., "Reduction of substance P after chronic antidepressants treatment in the striatum, substantia nigra and amygdala of the rat", Brain Res. 739: 70-78 (1996).

Stella et al., "Prodrugs Do they have advantages in clinical practice?" *Drugs*, 29:455-473 (1985).

Stella et al., "Prodrugs: the control of drug delivery via bioreversible chemical modification", *Drug Delivery Systems*, 112-176 (1985).

Tattersall et al., "Tachykinin $NK_1$ receptor antagonists act centrally to inhibit emesis induced by the chemotherapeutic agent cisplatin in ferrets", *Neuropharmacol*, 35:8, 1121-1129 (1996).

Tattersall et al., "The novel $NK_1$ receptor antagonist MK-0869 (L-754,030) and its water soluble phosphoryl prodrug, L-758,298, inhibit acute and delayed cisplatin-induced emesis in ferrets", *Neuropharmacology*, 39: 652-663 (2000).

Teixeira et al., "Effects of central administration of tachykinin receptor agonists and antagonists on plus-maze behavior in mice", *Eur. J. Pharmacol.* 311:7-14 (1996).

Tonini et al., "Tachykinin-dependent and independent component of peristalsis in the guinea pig isolated distal colon", *Gastroenterol.*, 120:938-945 (2001).

Watson et al., "The anti-emetic effects of CP-99,994 in the ferret and the dog: role of the $NK_1$ receptor", *Br. J. Pharmacol.* 115:84-94 (1995).

International Search Report re: PCT/EP2006/060419 dated Jun. 30, 2006.

* cited by examiner

SUBSTITUTED OXA-DIAZA-SPIRO-[5.5]-UNDECANONE DERIVATIVES AND THEIR USE AS NEUROKININ ANTAGONISTS

CROSS-REFERENCE TO RELATED APPLICATIONS

This application is the National Stage of International Application No. PCT/EP2006/060419, filed Mar. 3, 2006, which claims the benefit of EP Application No. 05101657.4, filed Mar. 3, 2005, the disclosures of which are incorporated herein by reference in their entireties for all purposes.

FIELD OF THE INVENTION

This invention concerns substituted oxa-diaza-spiro-[5.5]-undecanone derivatives having neurokinin antagonistic activity, in particular an $NK_1$ antagonistic activity, an $NK_3$ antagonistic activity, a combined $NK_1/NK_2$ antagonistic activity and a combined $NK_1/NK_2/NK_3$ antagonistic activity, their preparation, compositions comprising them and their use as a medicine, in particular for the treatment and/or prophylaxis of schizophrenia, emesis, anxiety and depression, irritable bowel syndrome (IBS), circadian rhythm disturbances, pre-eclampsia, nociception, pain, in particular visceral and neuropathic pain, pancreatitis, neurogenic inflammation, asthma, chronic obstructive pulmonary disease (COPD) and micturition disorders such as urinary incontinence.

BACKGROUND OF THE INVENTION

Tachykinins belong to a family of short peptides that are widely distributed in the mammalian central and peripheral nervous system (Bertrand and Geppetti, *Trends Pharmacol. Sci.* 17:255-259 (1996); Lundberg, *Can. J. Physiol. Pharmacol.* 73:908-914 (1995); Maggi, *Gen. Pharmacol.* 26:911-944 (1995); Regoli et al., *Pharmacol. Rev.* 46 (1994)). They share the common C-terminal sequence Phe-Xaa-Gly-Leu-Met-$NH_2$. Tachykinins released from peripheral sensory nerve endings are believed to be involved in neurogenic inflammation. In the spinal cord/central nervous system, tachykinins may play a role in pain transmission/perception and in some autonomic reflexes and behaviors. The three major tachykinins are Substance P (SP), Neurokinin A (NKA) and Neurokinin B (NKB) with preferential affinity for three distinct neurokinin receptor subtypes, termed $NK_1$, $NK_2$, and $NK_3$, respectively. However, functional studies on cloned receptors suggest strong functional cross-interaction between the 3 tachykinins and their corresponding neurokinin receptors (Maggi and Schwartz, *Trends Pharmacol. Sci.* 18: 351-355 (1997)).

Species differences in structure of $NK_1$ receptors are responsible for species-related potency differences of $NK_1$ antagonists (Maggi, *Gen. Pharmacol.* 26:911-944 (1995); Regoli et al., *Pharmacol. Rev.* 46(4):551-599 (1994)). The human $NK_1$ receptor closely resembles the $NK_1$ receptor of guinea-pigs and gerbils but differs markedly from the $NK_1$ receptor of rodents. The development of neurokinin antagonists has led to date to a series of peptide compounds of which might be anticipated that they are metabolically too labile to be employed as pharmaceutically active substances (Longmore J. et al., *DN&P* 8(1):5-23 (1995)).

The tachykinins are involved in schizophrenia, depression, (stress-related) anxiety states, emesis, inflammatory responses, smooth muscle contraction and pain perception. Neurokinin antagonists are in development for indications such as emesis, anxiety and depression, irritable bowel syndrome (IBS), circadian rhythm disturbances, visceral pain, neurogenic inflammation, asthma, micturition disorders, and nociception. In particular, $NK_1$ antagonists have a high therapeutic potential in emesis and depression and $NK_2$ antagonists have a high therapeutic potential in asthma treatments. $NK_3$ antagonists seem to play a role in the treatment of pain/inflammation (Giardina, G. et al. *Exp. Opin. Ther. Patents*, 10(6): 939-960 (2000)) and schizophrenia.

Schizophrenia

The $NK_3$ antagonist SR142801 (Sanofi) was recently shown to have antipsychotic activity in schizophrenic patients without affecting negative symptoms (Arvantis, L. *ACNP Meeting*, December 2001). Activation of $NK_1$ receptors causes anxiety, stressful events evoke elevated substance P (SP) plasma levels and $NK_1$ antagonists are reported to be anxiolytic in several animal models. The $NK_1$ antagonist from Merck, MK-869 shows antidepressant effects in major depression, but data were not conclusive due to a high placebo response rate. Moreover, the $NK_1$ antagonist from Glaxo-Welcome (S)-GR205,171 was shown to enhance dopamine release in the frontal cortex but not in the striatum (Lejeune et al. *Soc. Neurosci.*, November 2001). It is therefore hypothesized that $NK_3$ antagonism in combination with $NK_1$ antagonism would be beneficial against both positive and negative symptoms of schizophrenia.

Anxiety and Depression

Depression is one of the most common affective disorders of modern society with a high and still increasing prevalence, particularly in the younger members of the population. The life time prevalence rates of Major depression (MDD, DSM-IV) is currently estimated to be 10-25% for women and 5-12% for men, whereby in about 25% of patients the life time MDD is recurrent, without full inter-episode recovery and superimposed on dysthymic disorder. There is a high co-morbidity of depression with other mental disorders and, particularly in younger population high association with drug and alcohol abuse. In the view of the fact that depression primarily affects the population between 18-44 years of age e.g. the most productive population, it is obvious that it imposes a high burden on individuals, families and the whole society.

Among all therapeutic possibilities, the therapy with antidepressants is incontestably the most effective. A large number of antidepressants have been developed and introduced to the market in the course of the last 40 years. Nevertheless, none of the current antidepressants fulfill all criteria of an ideal drug (high therapeutic and prophylactic efficacy, rapid onset of action, completely satisfactory short- and long-term safety, simple and favourable pharmacokinetics) or is without side effects which in one or the other way limits their use in all groups and subgroups of depressed patients.

Since no treatment of the cause of depression exists at present, nor appears imminent, and no antidepressant is effective in more than 60-70% of patients; the development of a new antidepressant which may circumvent any of the disadvantages of the available drugs is justified.

Several findings indicate involvement of SP in stress-related anxiety states. Central injection of SP induces a cardiovascular response resembling the classical "fight or flight" reaction characterised physiologically by vascular dilatation in skeletal muscles and decrease of mesenteric and renal blood flow. This cardiovascular reaction is accompanied by a behavioural response observed in rodents after noxious stimuli or stress (Culman and Unger, *Can. J. Physiol. Pharmacol.* 73:885-891 (1995)). In mice, centrally administered $NK_1$ agonists and antagonists are anxiogenic and anxiolytic, respectively (Teixeira et al., *Eur. Pharmacol.* 311:7-14 (1996)). The ability of $NK_1$ antagonists to inhibit thumping induced by SP (or by electric shock; Ballard et al., *Trends Pharmacol. Sci.* 17:255-259 (2001)) might correspond to this antidepressant/anxiolytic activity, since in gerbils thumping plays a role as an alerting or warning signal to conspecifics.

The $NK_1$ receptor is widely distributed throughout the limbic system and fear-processing pathways of the brain, including the amygdala, hippocampus, septum, hypothalamus, and periaqueductal grey. Additionally, substance P is released centrally in response to traumatic or noxious stimuli and substance P-associated neuro-transmission may contribute to or be involved in anxiety, fear, and the emotional disturbances that accompany affective disorders such as depression and anxiety. In support of this view, changes in substance P content in discrete brain regions can be observed in response to stressful stimuli (Brodin et al., *Neuropeptides* 26:253-260 (1994)).

Central injection of substance P mimetics (agonists) induces a range of defensive behavioural and cardiovascular alterations including conditioned place aversion (Elliott, *Exp. Brain. Res.* 73:354-356 (1988)), potentiated acoustic startle response (Krase et al., *Behav. Brain. Res.* 63:81-88 (1994)), distress vocalisations, escape behaviour (Kramer et al., *Science* 281:1640-1645 (1998)) and anxiety on the elevated plus maze (Aguiar and Brandao, *Physiol. Behav.* 60:1183-1186 (1996)). These compounds did not modify motor performance and co-ordination on the rotarod apparatus or ambulation in an activity cage. Down-regulation of substance P biosynthesis occurs in response to the administration of known anxiolytic and antidepressant drugs (Brodin et al., *Neuropeptides* 26:253-260 (1994); Shirayama et al., *Brain. Res.* 739:70-78 (1996)). Similarly, a centrally administered $NK_1$ agonist-induced vocalisation response in guinea-pigs can be antagonised by antidepressants such as imipramine and fluoxetine as well as L-733,060, an $NK_1$ antagonist. These studies provide evidence suggesting that blockade of central $NK_1$ receptors may inhibit psychological stress in a manner resembling antidepressants and anxiolytics (Rupniak and Kramer, *Trends Pharmacol. Sci.* 20:1-12 (1999)), but without the side effects of present medications.

Emesis

Nausea and vomiting are among the most distressing side effects of cancer chemotherapy. These reduce the quality of life and may cause patients to delay or refuse, potentially curative drugs (Kris et al., *J. Clin. Oncol.*, 3:1379-1384 (1985)). The incidence, intensity and pattern of emesis is determined by different factors, such as the chemotherapeutic agent, dosage and route of administration. Typically, early or acute emesis starts within the first 4 h after chemotherapy administration, reaching a peak between 4 h and 10 h, and decreases by 12 to 24 h. Delayed emesis (developing after 24 h and continuing until 3-5 days post chemotherapy) is observed with most 'high-emetogenic' chemotherapeutic drugs (level 4 and 5 according to Hesketh et al., *J. Clin. Oncol.* 15:103 (1997)). In humans, these 'high-emetogenic' anti-cancer treatments, including cis-platinum, induce acute emesis in >98% and delayed emesis in 60-90% of cancer patients.

Animal models of chemotherapy such as cisplatin-induced emesis in ferrets (Rudd and Naylor, *Neuropharmacology* 33:1607-1608 (1994); Naylor and Rudd, *Cancer. Surv.* 21:117-135 (1996)) have successfully predicted the clinical efficacy of the $5-HT_3$ receptor antagonists. Although this discovery led to a successful therapy for the treatment of chemotherapy- and radiation-induced sickness in cancer patients, $5-HT_3$ antagonists such as ondansetron and granisetron (either or not associated with dexamethasone) are effective in the control of the acute emetic phase (the first 24 h) but can only reduce the development of delayed emesis (>24 h) with poor efficacy (De Mulder et al., *Annuals of Internal Medicine* 113:834-840 (1990); Roila, *Oncology* 50:163-167 (1993)). Despite these currently most effective treatments for the prevention of both acute and delayed emesis, still 50% of patients suffer from delayed vomiting and/or nausea (Antiemetic Subcommittee, *Annals Oncol.* 9:811-819 (1998)).

In contrast to $5-HT_3$ antagonists, $NK_1$ antagonists such as CP-99,994 (Piedimonte et al., *L. Pharmacol. Exp. Ther.* 266: 270-273 (1993)) and aprepitant (also known as MK-869 or L-754,030; Kramer et al., *Science* 281:1640-1645 (1998); Rupniak and Kramer, *Trends Pharmacol. Sci.* 20:1-12 (1999)) have now been shown to inhibit not only the acute but also the delayed phase of cisplatin-induced emesis in animals (Rudd et al., *Br. J. Pharmacol.* 119:931-936 (1996); Tattersall et al., *Neuropharmacology* 39:652-663 (2000)). $NK_1$ antagonists have also been demonstrated to reduce 'delayed' emesis in man in the absence of concomitant therapy (Cocquyt et al., *Eur. J. Cancer* 37:835-842 (2001); Navari et al., *N Engl. L. Med.* 340:190-195 (1999)). When administered together with dexamethasone and $5-HT_3$ antagonists, moreover, $NK_1$ antagonists (such as MK-869 and CJ-11,974, also known as Ezlopitant) have been shown to produce additional effects in the prevention of acute emesis (Campos et al., *J. Clin. Oncol.* 19:1759-1767 (2001); Hesketh et al., *Clin. Oncol.* 17:338-343 (1999)).

Central neurokinin $NK_1$ receptors play a major role in the regulation of emesis. $NK_1$ antagonists are active against a wide variety of emetic stimuli (Watson et al., *Br. J. Pharmacol.* 115:84-94 (1995); Tattersall et al., *Neuropharmacol.* 35:1121-1129 (1996); Megens et al., *J. Pharmacol. Exp. Ther.* 302:696-709 (2002)). The compounds are suggested to act by blocking central $NK_1$-receptors in the nucleus tractus solitarius. Apart from $NK_1$ antagonism, CNS penetration is thus a prerequisite for the antiemetic activity of these compounds. Loperamide-induced emesis in ferrets can be used as a fast and reliable screening model for the antiemetic activity of $NK_1$ antagonists. Further evaluation of their therapeutic value in the treatment of both the acute and the delayed phases of cisplatin-induced emesis has been demonstrated in the established ferret model (Rudd et al., *Br. J. Pharmacol.* 119: 931-936 (1994)). This model studies both 'acute' and 'delayed' emesis after cisplatin and has been validated in terms of its sensitivity to $5-HT_3$ receptor antagonists, glucocorticoids (Sam et al., *Eur. J. Pharmacol.* 417:231-237 (2001)) and other pharmacological challenges. It is unlikely that any future anti-emetic would find clinical acceptance unless successfully treating both the 'acute' and 'delayed' phases of emesis.

Viceral Pain and Irritable Bowel Syndrome (IBS)

Visceral sensation refers to all sensory information that originates in the viscera (heart, lungs, GI tract, hepatobiliary tract and urogenital tract), and is transmitted to the central nervous system resulting in conscious perception. Both the vagal nerve via the nodose ganglion and the primary sympathetic afferent nerves via dorsal root ganglias (DRG) and second order neurons in the dorsal horn serve as the initial pathways along which visceral sensory information is conveyed to the brain stem and to the viscero-somatic cortex. Visceral pain may be caused by neoplastic processes (e.g. pancreas cancer), inflammation (e.g. cholecystitis, peritonitis), ischemia and mechanical obstruction (e.g. urether stone).

The mainstay of medical treatment for visceral pain linked to organic disorders (in casu cancer of the viscera) still focuses on opiates.

Recent evidence suggests that non-organic visceral disorders such as irritable bowel syndrome (IBS), non-cardiac chest pain (NCCP) and chronic pelvic pain may originate from a state of "visceral hyperalgia". The latter is defined as a condition in which physiological, non-painful visceral stimuli (e.g. gut distension) lead to conscious perception of pain due to a decreased threshold for pain. Visceral hyperalgesia may reflect a state of a permanent, post-inflammatory resetting of the threshold for membrane depolarization at neuronal synapses within visceral sensory pathways. The initial inflammation may occur at the periphery (e.g. infectuous gastroenteritis) or at the site of visceral sensory information integration (neurogenic inflammation in the dorsal horn). Both SP and calcitonin gene-related peptide (CGRP) have been shown to act as pro-inflammatory neuropeptides in neurogenic inflammation.

Visceral hyperalgesia is currently considered as one of the prime targets for drug development aimed at treating functional bowel diseases, which occur in 15 to 25% of the western population. They constitute an enormous socio-economic problem in terms of medical care costs, prescription costs and absenteism. Current treatment options include anti-spasmodics (IBS and NCCP), promotility agents (e.g. tegasorod in constipation-IBS), laxatives (constipation-IBS), and loperamide (diarrhea-IBS), amongst others. None of these approaches has been shown to be very effective, particularly in treating pain. Low dose tricyclic antidepressants and SSRIs are used to treat visceral hyperalgesia in pain-predominant IBS, but both classes of compounds may have considerable effects on colonic transit. Ongoing research in this field has identified a considerable number of molecular targets that could serve for drug development in visceral hyperalgesia. These include NK receptors, the CGRP receptor, 5-HT$_3$ receptors, glutamate receptors, and the kappa opioid receptor. Ideally, a "visceral analgesic compound" should block heightened sensory transfer from the viscera to the CNS without affecting the normal physiological homeostasis of the GI tract with regards to propulsive motor activity, absorption and secretion, and sensation. There is compelling evidence linking tachykinin to visceral nociceptive signalling. A number of pre-clinical publications on the role of $NK_1$, $NK_2$ and $NK_3$ receptors in visceral pain and visceral hyperalgesia indicate a discrepancy between the implication of $NK_1$, $NK_2$ and $NK_3$ receptors in the different inflammation hypersensitivity rodent models. Recently, Kamp et al., *J. Pharmacol. Exp. Ther.* 299:105-113 (2001) suggested that a combined neurokinin receptor antagonist could be more active than a selective neurokinin receptor antagonist. Substance P and $NK_1$, $NK_2$ and $NK_3$ receptors are elevated in clinical pain states, including visceral pain states (Lee et al., *Gastroenterol.* 118: A846 (2000)). Given the recent failures of $NK_1$ receptor antagonists as an analgesic in human pain trials (Goldstein et al., *Clin. Pharm. Ther.* 67:419-426 (2000)), combinations of antagonists may be necessary to have a significant clinical effect. $NK_3$ receptor antagonists are anti-hyperalgesic (Julia et al., *Gastroenterol.* 116:1124-1131 (1999); *J. Pharmacol. Exp. Ther.* 299:105-113 (2001)). Recently, the involvement of $NK_1$ and $NK_3$ receptors but not $NK_2$ receptors at spinal level was demonstrated in visceral hypersensitivity mediated by nociceptive and non-nociceptive afferent inputs (Gaudreau & Ploudre, *Neurosci. Lett.* 351:59-62 (2003). Combining the $NK_{1-2-3}$ antagonistic activity could therefore represent an interesting therapeutic target for the development of novel treatments for visceral hyperalgesia.

A reasonable number of pre-clinical publications over the role of $NK_1$ receptors in visceral pain has been published. Using $NK_1$ receptor knockout mice and $NK_1$ antagonists in animal models, different groups have demonstrated the important role played by the $NK_1$ receptor in hyperalgesia and visceral pain. The distribution of $NK_1$ receptors and substance P favours a major role in visceral rather than in somatic pain. Indeed more than 80% of visceral primary afferent contain substance P compared with only 25% skin afferents. $NK_1$ receptors are also involved in gastrointestinal motility (Tonini et al., *Gastroenterol.* 120:938-945 (2001); Okano et al., *J. Pharmacol. Exp. Ther.* 298:559-564 (2001)). Because of this dual role in both gastrointestinal motility and in nociception, $NK_1$ antagonists are considered to have potential to ameliorate symptoms in IBS patients.

Urinary Incontinence

Urge urinary incontinence is caused by urinary bladder or detrusor hyperreflexia ("irritable bladder"). This hyperreflexia relates to hyperexcitability of bladder sensory afferent C-fibers projecting to the spinal cord. The origin of C-fiber hyperexcitability is multifactorial but occurs for example after bladder infection and chronic distention of the bladder wall (eg. benign prostate hypertrophy, BPH). Hence, treatment should be aimed at decreasing neuronal hyperexcitability. Intravesical instillation of vanilloids (eg. capsaicin) results in a long-term beneficial effect on detrusor hyperreflexia refractory to conventional treatment with anticholinergic drugs. Analogous to animal studies, the effect of vanilloids is mediated through a neurotoxic effect on sensory nerve terminals. In human bladder, subendothelial sensory nerves contain tachykinins, which drive detrusor hyperexcitability. The NK receptors involved in this effect are peripheral $NK_2$ receptors and to a lesser extent, also $NK_1$ receptors. The latter are claimed to play a role in bladder hyperreflexia at the level of the spinal cord. As a consequence, a centrally acting $NK_1$/peripherally acting $NK_2$ antagonist is preferred for the treatment of detrusor hyperexcitability. Interestingly, activation of $NK_2$ receptors increases aromatase activity in Sertoli cells. $NK_2$ receptor antagonists reduce serum testosterone levels in mice, and this may be of therapeutic importance in BPH.

BACKGROUND PRIOR ART

Compounds containing a piperidinyl-moiety, substituted by a piperidinyl or pyrrolidinyl-moiety were published in WO97/24324 (Jul. 10, 1997), WO 97/24350 (Jul. 10, 1997) and WO97/24356 (Jul. 10, 1997), all by Janssen Pharmaceutica N.V. for use as substance P (neurokinin) antagonists. Compounds comprising a substituted diaza-spiro[4.5] decanyl-moiety were published in WO01/94346 (Dec. 13, 2001) by F. Hoffmann-La Roche AG for use as neurokinin receptor antagonists.

The compounds of the present invention differ structurally from the compounds of the prior art in that the compounds of the present invention all comprise a piperidinyl-moiety substituted with a oxa-diaza-spiro[5.5] undecanone moiety as well as in their improved ability as potent, orally and centrally active neurokinin antagonists with therapeutic value, especially for the treatment and/or prophylaxis of schizophrenia, emesis, anxiety and depression, irritable bowel syndrome (IBS), circadian rhythm disturbances, pre-eclampsia, nociception, pain, in particular visceral and neuropathic pain, pancreatitis, neurogenic inflammation, asthma, chronic obstructive pulmonary disease (COPD) and micturition disorders such as urinary incontinence.

SUMMARY OF THE INVENTION

The present invention relates to novel substituted oxa-diaza-spiro-[5.5]-undecanone derivatives according to the general Formula (I)

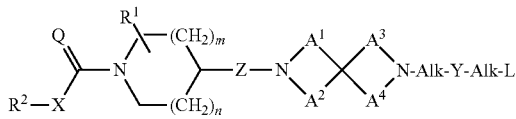
(I)

the pharmaceutically acceptable acid or base addition salts thereof, the stereochemically isomeric forms thereof, the N-oxide form thereof and prodrugs thereof, wherein:

$R^2$ is $Ar^2$, $Ar^2$-alkyl, di($Ar^2$)alkyl, $Het^1$ or $Het^1$-alkyl;

X is a covalent bond or a bivalent radical of formula —O—, —S— or —$NR^3$—;

Q is O or $NR^3$;

each $R^3$ independently from each other, is hydrogen or alkyl;

$R^1$ is selected from the group of $Ar^1$, $Ar^1$-alkyl and di($Ar^1$)-alkyl;

n is an integer, equal to 0, 1 or 2;

m is an integer, equal to 1 or 2, provided that if m is 2, then n is 1;

Z is a covalent bond or a bivalent radical of formula —$CH_2$— or >C(=O);

$A^1$, $A^2$, $A^3$ and $A^4$ are each independently from each other selected from the group of —$CH_2CH_2$—, —C(=O)O— and —OC(=O)—, provided that at least one of —C(=O)O— and —OC(=O)— is selected and that =O is in an alpha-position relative to the N-atom;

each Alk represents, independently from each other, a covalent bond; a bivalent straight or branched, saturated or unsaturated hydrocarbon radical having from 1 to 6 carbon atoms; or a cyclic saturated or unsaturated hydrocarbon radical having from 3 to 6 carbon atoms; each radical optionally substituted on one or more carbon atoms with one or more, phenyl, halo, cyano, hydroxy, formyl and amino radicals;

Y is a covalent bond or a bivalent radical of formula —C(=O)—, —$SO_2$—>C=CH—R or >C=N—R, wherein R is H, CN or nitro;

L is selected from the group of hydrogen, alkyl, alkenyl, alkyloxy, alkyloxyalkyloxy, alkylcarbonyloxy, alkyloxycarbonyl, mono- and di(alkyl)amino, mono- and di(alkyloxycarbonyl)amino, mono- and di(alkylcarbonyl)amino, mono- and di($Ar^3$)amino, mono- and di($Ar^3$alkyl)amino, mono- and di($Het^2$)amino, mono- and di($Het^2$alkyl)amino, alkylsulfonyl, norbornyl, adamantyl, tricycloundecyl, $Ar^3$, $Ar^3$-oxy, $Ar^3$-carbonyl, $Het^2$, Het-oxy, $Het^2$-carbonyl and mono- and di($Het^2$carbonyl)amino;

$Ar^1$ is phenyl, optionally substituted with 1, 2 or 3 substituents, each independently from each other, selected from the group of halo, alkyl, cyano, aminocarbonyl and alkyloxy;

$Ar^2$ is naphthalenyl or phenyl, each optionally substituted with 1, 2 or 3 substituents, each independently from each other, selected from the group of halo, nitro, amino, mono- and di(alkyl)amino, cyano, alkyl, hydroxy, alkyloxy, carboxyl, alkyloxycarbonyl, aminocarbonyl and mono- and di(alkyl)aminocarbonyl;

$Ar^3$ is naphthalenyl or phenyl, optionally substituted with 1, 2 or 3 substituents, each independently from each other, selected from the group of alkyloxy, alkylcarbonylamino, methane sulfonyl, $Ar^1$carbonyloxyalkyl, $Ar^1$alkyloxycarbonyl, $Ar^1$alkyloxyalkyl, alkyl, halo, hydroxy, pyridinyl, morpholinyl, pyrrolyl, pyrrolidinyl, imidazo[1,2-a]pyridinyl, morpholinylcarbonyl, pyrrolidinylcarbonyl, amino and cyano;

$Het^1$ is a monocyclic heterocyclic radical selected from the group of pyrrolyl, pyrazolyl, imidazolyl, furanyl, thienyl, oxazolyl, isoxazolyl, thiazolyl, isothiazolyl, pyridinyl, pyrimidinyl, pyrazinyl and pyridazinyl; or a bicyclic heterocyclic radical selected from the group of quinolinyl, quinoxalinyl, indolyl, benzimidazolyl, benzoxazolyl, benzisoxazolyl, benzothiazolyl, benzisothiazolyl, benzofuranyl, benzothienyl, indanyl and chromenyl; wherein each mono- and bicyclic heterocyclic radical may optionally be substituted on any atom by one or more radicals, each independently from each other, selected from the group of halo, oxo and alkyl;

$Het^2$ is a monocyclic heterocyclic radical selected from the group of pyrrolidinyl, dihydro-2H-pyranyl, pyranyl, dioxolyl, imidazolidinyl, tetrahydropyridinyl, tetrahydropyrimidinyl, pyrazolidinyl, piperidinyl, morpholinyl, dithianyl, thiomorpholinyl, piperazinyl, imidazolidinyl, tetrahydrofuranyl, 2H-pyrrolyl, pyrrolinyl, imidazolinyl, pyrazolinyl, pyrrolyl, imidazolyl, pyrazolyl, triazolyl, furanyl, thienyl, oxazolyl, dioxazolyl, oxazolidinyl, isoxazolyl, thiazolyl, thiadiazolyl, isothiazolyl, pyridinyl, pyrimidinyl, pyrazinyl, pyridazinyl, triazinyl and tetrazolyl;

or a bicyclic heterocyclic radical selected from the group of 2,3-dihydro-benzo[1,4] dioxine, octahydro-benzo[1,4] dioxine, octabicycloheptyl, benzopiperidinyl, quinolinyl, quinoxalinyl, indolyl, isoindolyl, chromanyl, benzimidazolyl, imidazo[1,2-a]pyridinyl, benzoxazolyl, benzodioxolyl, benzisoxazolyl, benzoxadiazolyl, benzothiazolyl, benzisothiazolyl, benzofuranyl, dihydroisobenzofuranyl, or benzothienyl; wherein each mono-, and bicyclic heterocyclic radical may optionally be substituted on any atom with one or more radicals selected from the group of $Ar^1$, $Ar^1$alkyl, $Ar^1$alkyloxyalkyl, halo, hydroxy, alkyl, piperidinyl, pyrrolyl, thienyl, oxo, alkyloxy, alkylcarbonyl, $Ar^1$carbonyl, mono- and di(alkyl)aminoalkyl, alkyloxyalkyl and alkyloxycarbonyl;

alkyl is a straight or branched saturated hydrocarbon radical having from 1 to 6 carbon atoms or a cyclic saturated hydrocarbon radicals having from 3 to 6 carbon atoms; each hydrocarbon radical optionally substituted on one or more carbon atoms with one or more radicals selected from the group of phenyl, halo, trihalomethyl, aminocarbonyl, methyl, ethyl, propyl, isopropyl, t-butyl, cyano, oxo, hydroxy, formyl and amino; and alkenyl is a straight or branched unsaturated hydrocarbon radical having from 1 to 6 carbon atoms and having 1 or more unsaturated bonds; or a cyclic unsaturated hydrocarbon radical having from 3 to 6 carbon atoms and having 1 or more unsaturated bonds; each hydrocarbon radical optionally substituted on one or more carbon atoms with one or more radicals selected from the group of phenyl, halo, cyano, oxo, hydroxy, formyl and amino.

The invention further relates to a compound according to the general Formula (I), the pharmaceutically acceptable acid or base addition salts thereof, the stereochemically isomeric forms thereof, the N-oxide form thereof and a prodrug thereof, as a medicine.

The invention further relates to compositions comprising a compound according to the general Formula (I), the pharmaceutically acceptable acid or base addition salts thereof, the stereochemically isomeric forms thereof, the N-oxide form thereof and a prodrug thereof, as well as to processes for the preparation of said compounds and said compositions according to the invention.

The invention further relates to the use of a compound according to the general Formula (I), the pharmaceutically acceptable acid or base addition salts thereof, the stereochemically isomer for the manufacture of a medicament for treating tachykinin mediated conditions, in particular for the treatment and/or prophylaxis of schizophrenia, emesis, anxiety and depression, irritable bowel syndrome (IBS), circadian rhythm disturbances, pre-eclampsia, nociception, pain, in particular visceral and neuropathic pain, pancreatitis, neurogenic inflammation, asthma, chronic obstructive pulmonary disease (COPD) and micturition disorders such as urinary incontinence.

DETAILED DESCRIPTION OF THE INVENTION

In particular, the invention relates to a compound according to the general Formula (I), the pharmaceutically acceptable acid or base addition salts thereof, the stereochemically isomeric forms thereof, the N-oxide form thereof and a prodrug thereof, wherein the spiro-moiety has one of the following chemical structures according to any one of formulas (f1) to (f5), wherein all variables are defined as in Formula (I) and "a" denotes the piperidinyl-moiety of Formula (I) and "b" denotes the Alk-Y-Alk-L-moiety of Formula (I).

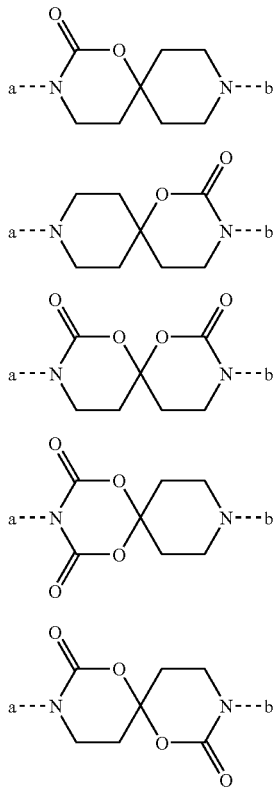

More in particular, the invention relates to a compound according to the general Formula (I), the pharmaceutically acceptable acid or base addition salts thereof, the stereochemically isomeric forms thereof, the N-oxide form thereof and a prodrug thereof, wherein the spiro-moiety has the Formula (f1) or (f2), wherein the variables are defined as in Formula (I) and "a" denotes the piperidinyl-moiety of Formula (I) and "b" denotes the Alk-Y-Alk-L-moiety of Formula (I).

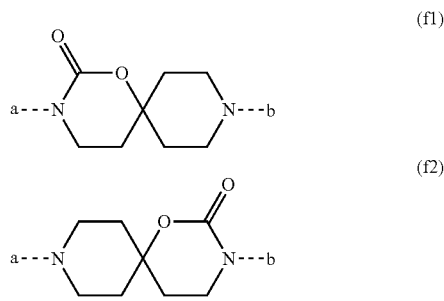

More in particular, the invention relates to a compound according to the general Formula (I), the pharmaceutically acceptable acid or base addition salts thereof, the stereochemically isomeric forms thereof, the N-oxide form thereof and a prodrug thereof, wherein $R^1$ is benzyl and attached to the 2-position or $R^1$ is phenyl and attached to the 3-position, as exemplified in either of the following formulas for compounds according to Formula (I) wherein m and n are equal to 1.

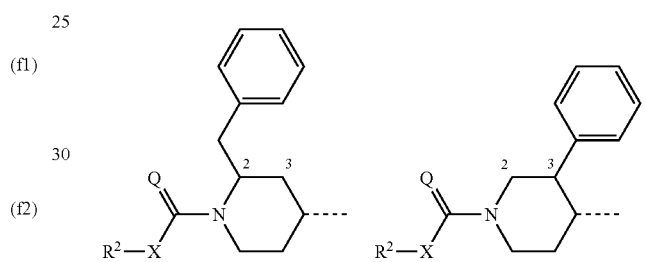

More in particular, the invention relates to a compound according to the general Formula (I), the pharmaceutically acceptable acid or base addition salts thereof, the stereochemically isomeric forms thereof, the N-oxide form thereof and a prodrug thereof, wherein the $R^2$—X—C(=Q)-moiety is 3,5-di-(trifluoromethyl)phenylcarbonyl.

More in particular, the invention relates to a compound according to the general Formula (I), the pharmaceutically acceptable acid or base addition salts thereof, the stereochemically isomeric forms thereof, the N-oxide form thereof and a prodrug thereof, wherein m and n are both equal to 1.

More in particular, the invention relates to a compound according to the general Formula (I), the pharmaceutically acceptable acid or base addition salts thereof, the stereochemically isomeric forms thereof, the N-oxide form thereof and a prodrug thereof, wherein Z is a covalent bond.

More in particular, the invention relates to a compound according to the general Formula (I), the pharmaceutically acceptable acid or base addition salts thereof, the stereochemically isomeric forms thereof, the N-oxide form thereof and a prodrug thereof, wherein Y is a covalent bond or —C(=O)—.

More in particular, the invention relates to a compound according to the general Formula (I), the pharmaceutically acceptable acid or base addition salts thereof, the stereochemically isomeric forms thereof, the N-oxide form thereof and a prodrug thereof, wherein each Alk independently from each other is a covalent bond or —CH$_2$—.

More in particular, the invention relates to a compound according to the general Formula (I), the pharmaceutically acceptable acid or base addition salts thereof, the stereochemically isomeric forms thereof, the N-oxide form thereof and a prodrug thereof, wherein L is selected from the group of hydrogen, isopropyl, pentyl, cyclopropyl, cyclohexyl, tetrahydrofuranyl, pyrrolyl, furanyl, thienyl, thiadiazolyl, phenyl, pyridinyl and pyrazinyl. Preferentially, L is cyclopropyl.

More in particular, the invention relates to a compound according to the general Formula (I), the pharmaceutically acceptable acid or base addition salts thereof, the stereochemically isomeric forms thereof, the N-oxide form thereof and a prodrug thereof, wherein:
  $R^2$ is phenyl, optionally substituted with 1, 2 or 3 haloalkyl substituents;
  X is a covalent bond;
  Q is O;
  $R^1$ is phenyl or benzyl;
  n is an integer, equal to 1;
  m is an integer, equal to 1;
  Z is a covalent bond;
  $A^1$, $A^2$, $A^3$ and $A^4$ are each independently from each other selected from the group of —$CH_2CH_2$—, —C(=O)O— and —OC(=O)—, provided that at least one of —C(=O)O— and —OC(=O)— is selected and that =O is in an alpha-position relative to the N-atom;
  t is an integer, equal to 0;
  each Alk represents, independently from each other, a covalent bond or a bivalent straight, saturated hydrocarbon radical having from 1 to 2 carbon atoms;
  Y is a covalent bond or a bivalent radical of formula —C(=O)—;
  L is selected from the group of hydrogen, alkyl, $Ar^3$ and $Het^2$;
  $Ar^3$ is phenyl, optionally substituted with a substituent, selected from the group of alkyl, halo and hydroxy;
  $Het^2$ is a monocyclic heterocyclic radical selected from the group of tetrahydrofuranyl, pyrrolyl, furanyl, thienyl, thiadiazolyl, pyridinyl and pyrazinyl; wherein each monocyclic heterocyclic radical may optionally be substituted on any atom with one or more alkyl-radicals; and
  alkyl is a straight or branched saturated hydrocarbon radical having from 1 to 6 carbon atoms or a cyclic saturated hydrocarbon radicals having from 3 to 6 carbon atoms.

More in particular, the invention relates to a compound according to the general Formula (I), the pharmaceutically acceptable acid or base addition salts thereof, the stereochemically isomeric forms thereof, the N-oxide form thereof and a prodrug thereof, wherein the compound is a compound with compound number 1.4, as described in this application, in particular in any one of the tables, in particular in any one of Tables 1-2.

In the framework of this application, alkyl is defined as a monovalent straight or branched saturated hydrocarbon radical having from 1 to 6 carbon atoms, for example methyl, ethyl, propyl, butyl, 1-methylpropyl, 1,1-dimethylethyl, pentyl, hexyl; alkyl further defines a monovalent cyclic saturated hydrocarbon radical having from 3 to 6 carbon atoms, for example cyclopropyl, methylcyclopropyl, cyclobutyl, cyclopentyl and cyclohexyl. The definition of alkyl also comprises an alkyl radical that is optionally substituted on one or more carbon atoms with one or more phenyl, halo, cyano, oxo, hydroxy, formyl and amino radicals, for example hydroxyalkyl, in particular hydroxymethyl and hydroxyethyl and polyhaloalkyl, in particular difluoromethyl and trifluoromethyl.

In the framework of this application, halo is generic to fluoro, chloro, bromo and iodo.

In the framework of this application, with "compounds according to the invention" is meant a compound according to the general Formula (I), the pharmaceutically acceptable acid or base addition salts thereof, the stereochemically isomeric forms thereof, the N-oxide form thereof and a prodrug thereof.

In the framework of this application, especially in the moiety $Alk^a$-Y-$Alk^b$ in Formula (I), when two or more consecutive elements of said moiety denote a covalent bond, then a single covalent bond is denoted. For example, when $Alk^a$ and Y denote both a covalent bond and $Alk^b$ is —$CH_2$—, then the moiety $Alk^a$-Y-$Alk^b$ denotes —$CH_2$—. Similarly, if $Alk^a$, Y and $Alk^b$ each denote a covalent bond and L denotes H, then the moiety $Alk^a$-Y-$Alk^b$-L denotes —H.

The pharmaceutically acceptable salts are defined to comprise the therapeutically active non-toxic acid addition salts forms that the compounds according to Formula (I) are able to form. Said salts can be obtained by treating the base form of the compounds according to Formula (I) with appropriate acids, for example inorganic acids, for example hydrohalic acid, in particular hydrochloric acid, hydrobromic acid, sulfuric acid, nitric acid and phosphoric acid; organic acids, for example acetic acid, hydroxyacetic acid, propanoic acid, lactic acid, pyruvic acid, oxalic acid, malonic acid, succinic acid, maleic acid, fumaric acid, malic acid, tartaric acid, citric acid, methanesulfonic acid, ethanesulfonic acid, benzenesulfonic acid, p-toluenesulfonic acid, cyclamic acid, salicylic acid, p-aminosalicylic acid and pamoic acid.

The compounds according to Formula (I) containing acidic protons may also be converted into their therapeutically active non-toxic metal or amine addition salts forms by treatment with appropriate organic and inorganic bases. Appropriate base salts forms comprise, for example, the ammonium salts, the alkaline and earth alkaline metal salts, in particular lithium, sodium, potassium, magnesium and calcium salts, salts with organic bases, e.g. the benzathine, N-methyl-D-glucamine, hybramine salts, and salts with amino acids, for example arginine and lysine.

Conversely, said salts forms can be converted into the free forms by treatment with an appropriate base or acid.

The term addition salt as used in the framework of this application also comprises the solvates that the compounds according to Formula (I) as well as the salts thereof, are able to form. Such solvates are, for example, hydrates and alcoholates.

The N-oxide forms of the compounds according to Formula (I) are meant to comprise those compounds of Formula (I) wherein one or several nitrogen atoms are oxidized to the so-called N-oxide, particularly those N-oxides wherein one or more tertiary nitrogens (e.g of the piperazinyl or pyrrolidinyl radical) are N-oxidized. Such N-oxides can easily be obtained by a skilled person without any inventive skills and they are obvious alternatives for the compounds according to Formula (I) since these compounds are metabolites, which are formed by oxidation in the human body upon uptake. As is generally known, oxidation is normally the first step involved in drug metabolism (Textbook of Organic Medicinal and Pharmaceutical Chemistry, 1977, pages 70-75). As is also generally known, the metabolite form of a compound can also be administered to a human instead of the compound per se, with possibly the same effects.

The compounds according to the invention possess at least 2 oxydizable nitrogens (tertiary amines moieties). It is therefore highly likely that N-oxides will form in the human metabolism.

The compounds of Formula (I) may be converted to the corresponding N-oxide forms following art-known procedures for converting a trivalent nitrogen into its N-oxide form. Said N-oxidation reaction may generally be carried out by reacting the starting material of Formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tertbutyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

The term "stereochemically isomeric forms" as used hereinbefore defines all the possible isomeric forms that the compounds of Formula (I) may possess. Unless otherwise mentioned or indicated, the chemical designation of compounds denotes the mixture of all possible stereochemically isomeric forms having that designation, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration. Compounds encompassing double bonds can have an E or Z-stereochemistry at said double bond. Stereochemically isomeric forms of the compounds of Formula (I) are obviously intended to be embraced within the scope of this invention.

Following CAS nomenclature conventions, when two stereogenic centers of known absolute configuration are present in a molecule, an R or S descriptor is assigned (based on Cahn-Ingold-Prelog sequence rule) to the lowest-numbered chiral center, the reference center. R* and S* each indicate optically pure stereogenic centers with undetermined absolute configuration. If "α" and "β" are used: the position of the highest priority substituent on the asymmetric carbon atom in the ring system having the lowest ring number, is arbitrarily always in the "α" position of the mean plane determined by the ring system. The position of the highest priority substituent on the other asymmetric carbon atom in the ring system (hydrogen atom in compounds according to Formula (I)) relative to the position of the highest priority substituent on the reference atom is denominated "α", if it is on the same side of the mean plane determined by the ring system, or "β", if it is on the other side of the mean plane determined by the ring system.

Compounds according to Formula (I) and some of the intermediate compounds have at least two stereogenic centers in their structure.

The invention also comprises derivative compounds (usually called "pro-drugs") of the pharmacologically-active compounds according to the invention, which are degraded in vivo to yield the compounds according to the invention. Prodrugs are usually (but not always) of lower potency at the target receptor than the compounds to which they are degraded. Pro-drugs are particularly useful when the desired compound has chemical or physical properties that make its administration difficult or inefficient. For example, the desired compound may be only poorly soluble, it may be poorly transported across the mucosal epithelium, or it may have an undesirably short plasma half-life. Further discussion on pro-drugs may be found in Stella, V. J. et al., "Prodrugs", *Drug Delivery Systems,* 1985, pp. 112-176, and *Drugs,* 1985, 29, pp. 455-473.

Pro-drugs forms of the pharmacologically-active compounds according to the invention will generally be compounds according to Formula (I), the pharmaceutically acceptable acid or base addition salts thereof, the stereochemically isomeric forms thereof and the N-oxide form thereof, having an acid group which is esterified or amidated. Included in such esterified acid groups are groups of the formula —COOR$^x$, where R$^x$ is a C$_{1-6}$alkyl, phenyl, benzyl or one of the following groups:

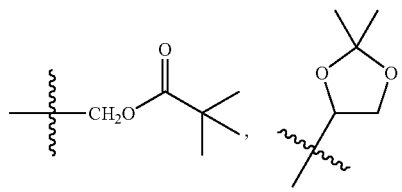

Amidated groups include groups of the formula —CONR$^y$R$^z$, wherein R$^y$ is H, C$_{1-6}$alkyl, phenyl or benzyl and R$^z$ is —OH, H, C$_{1-6}$alkyl, phenyl or benzyl. Compounds according to the invention having an amino group may be derivatised with a ketone or an aldehyde such as formaldehyde to form a Mannich base. This base will hydrolyze with first order kinetics in aqueous solution.

The compounds of Formula (I) as prepared in the processes described below may be synthesized in the form of racemic mixtures of enantiomers that can be separated from one another following art-known resolution procedures. The racemic compounds of Formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

Pharmacology

Substance P and other tachykinins are involved in a variety of biological actions such as pain transmission (nociception), neurogenic inflammation, smooth muscle contraction, plasma protein extravasation, vasodilation, secretion, mast cell degranulation, and also in activation of the immune system. A number of diseases are deemed to be engendered by activation of neurokinin receptors, in particular the NK$_1$ receptor, by excessive release of substance P and other neurokinins in particular cells such as cells in the neuronal plexi of the gastrointestinal tract, unmyelinated primary sensory afferent neurons, sympathetic and parasympathetic neurons and nonneuronal cell types (DN&P 8(1):5-23 (1995) and Longmore J. et al., "Neurokinin Receptors" *Pharmacological Reviews* 46(4):551-599 (1994)).

The compounds of the present invention are potent inhibitors of neurokinin-mediated effects, in particular those mediated via the NK$_1$, NK$_2$ and NK$_3$ receptor, and may therefore be described as neurokinin antagonists, especially as substance P antagonists, as may be indicated in vitro by the antagonism of substance P-induced relaxation of pig coronary arteries. The binding affinity of the present compounds for the human, guinea-pig and gerbil neurokinin receptors may also be determined in vitro in a receptor binding test using $^3$H-substance-P as radioligand. The subject compounds also show substance-P antagonistic activity in vivo as may be evidenced by, for instance, the antagonism of substance P-induced plasma extravasation in guinea-pigs, or the antagonism of drug-induced emesis in ferrets (Watson et al., *Br. J. Pharmacol.* 115:84-94 (1995)).

In view of their capability to antagonize the actions of tachykinins by blocking the neurokinin receptors, and in particular by blocking the $NK_1$, $NK_2$ and $NK_3$ receptor, the compounds according to the invention are useful as a medicine, in particular in the prophylactic and therapeutic treatment of tachykinin-mediated conditions. In particular are compounds according to the invention are useful as orally active, centrally penetrating medicines in the prophylactic and therapeutic treatment of tachykinin-mediated conditions.

More in particular, it has been found that some compounds exhibit a combined $NK_1/NK_2$ antagonistic activity and a combined $NK_1/NK_2/NK_3$ antagonistic activity as can be seen from the table in experimental section.

The invention therefore relates to a compound according to the general Formula (I), the pharmaceutically acceptable acid or base addition salts thereof, the stereochemically isomeric forms thereof, the N-oxide form thereof and prodrugs thereof, for use as a medicine.

The invention also relates to the use of a compound according to the general Formula (I), the pharmaceutically acceptable acid or base addition salts thereof, the stereochemically isomeric forms thereof, the N-oxide form thereof and prodrugs thereof for the manufacture of a medicament for treating, either prophylactic or therapeutic or both, tachykinin mediated conditions.

The compounds according to the invention are useful in the treatment of CNS disorders, in particular schizoaffective disorders; depression; anxiety disorders; stress-related disorders; sleep disorders; cognitive disorders; personality disorders; eating disorders; neurodegenerative diseases; addiction disorders; mood disorders; sexual dysfunction; visceral pain and other CNS-related conditions; inflammation; allergic disorders; emesis; gastrointestinal disorders, in particular irritable bowel syndrome (IBS); skin disorders; vasospastic diseases; fibrosing and collagen diseases; disorders related to immune enhancement or suppression; rheumatic diseases; and body weight control.

In particular, the compounds according to the invention are useful in the treatment or prevention of schizoaffective disorders resulting from various causes, including schizoaffective disorders of the manic type, of the depressive type and of the mixed type; paranoid, disorganized, catatonic, undifferentiated and residual schizophrenia; schizophreniform disorder; delusional disorder; brief psychotic disorder; shared psychotic disorder; substance-induced psychotic disorder; and psychotic disorder not otherwise specified.

In particular, the compounds according to the invention are useful in the treatment or prevention of depression including but not limited to major depressive disorders including bipolar depression; unipolar depression; single or recurrent major depressive episodes with or without psychotic features, catatonic features, melancholic features, atypical features or postpartum onset, and, in the case of recurrent episodes, with or without seasonal pattern. Other mood disorders encompassed within the term "major depressive disorder" include dysthymic disorder with early or late onset and with or without atypical features; bipolar I disorder; bipolar II disorder; cyclothymic disorder; recurrent brief depressive disorder; mixed affective disorder; neurotic depression; post traumatic stress disorder and social phobia; dementia of the Alzheimer's type with early or late onset or with depressed mood; vascular dementia with depressed mood; substance-induced mood disorders such as mood disorders induced by alcohol, amphetamines, cocaine, hallucinogens, inhalants, opioids, phencyclidine, sedatives, hypnotics, anxiolytics and other substances; schizoaffective disorder of the depressed type; and adjustment disorder with depressed mood. Major depressive disorders may also result from a general medical condition including, but not limited to, myocardial infarction, diabetes, miscarriage or abortion, etc.

In particular, the compounds according to the invention are useful in the treatment or prevention of anxiety disorders, including but not limited to panic attack; agoraphobia; panic disorder without agoraphobia; agoraphobia without history of panic disorder; specific phobia; social phobia; obsessive-compulsive disorder; post-traumatic stress disorder; acute stress disorder; generalized anxiety disorder; anxiety disorder due to a general medical condition; substance-induced anxiety disorder; and anxiety disorder not otherwise specified.

In particular, the compounds according to the invention are useful in the treatment or prevention of stress-related disorders associated with depression and/or anxiety, including but not limited to acute stress reaction; adjustment disorders, such as brief depressive reaction and prolonged depressive reaction; mixed anxiety and depressive reaction; adjustment disorder with predominant disturbance of other emotions; adjustment disorder with predominant disturbance of conduct; adjustment disorder with mixed disturbance of emotions and conduct; adjustment disorders with other specified predominant symptoms; and other reactions to severe stress.

In particular, the compounds according to the invention are useful in the treatment or prevention of sleep disorders, including but not limited to dysomnia and/or parasomnias as primary sleep disorders; insomnia; sleep apnea; narcolepsy; circadian rhythms disorders; sleep disorders related to another mental disorder; sleep disorder due to a general medical condition; and substance-induced sleep disorder.

In particular, the compounds according to the invention are useful in the treatment or prevention of cognitive disorders, including but not limited to dementia; amnesic disorders and cognitive disorders not otherwise specified, especially dementia caused by degenerative disorders, lesions, trauma, infections, vascular disorders, toxins, anoxia, vitamin deficiency or endocrinic disorders; dementia of the Alzheimer's type, with early or late onset or with depressed mood; AIDS-associated dementia or amnesic disorders caused by alcohol or other causes of thiamin deficiency, bilateral temporal lobe damage due to Herpes simplex encephalitis and other limbic encephalitis, neuronal loss secondary to anoxia/hypoglycemia/severe convulsions and surgery, degenerative disorders, vascular disorders or pathology around ventricle III. Furthermore, the compounds according to the invention are also useful as memory and/or cognition enhancers in healthy humans with no cognitive and/or memory deficit.

In particular, the compounds according to the invention are useful in the treatment or prevention of personality disorders, including but not limited to paranoid personality disorder; schizoid personality disorder; schizotypical personality disorder; antisocial personality disorder; borderline personality disorder; histrionic personality disorder; narcissistic personality disorder; avoidant personality disorder; dependent personality disorder; obsessive-compulsive personality disorder and personality disorder not otherwise specified.

In particular, the compounds according to the invention are also useful in the treatment or prevention of eating disorders, including anorexia nervosa; atypical anorexia nervosa; bulimia nervosa; atypical bulimia nervosa; overeating associated with other psychological disturbances; vomiting associated with other psychological disturbances; and non-specified eating disorders.

In particular, the compounds according to the invention are also useful in the treatment or prevention of neurodegenerative diseases, including but not limited to Alzheimer's disease; Huntington's chorea; Creutzfeld-Jacob disease; Pick's disease; demyelinating disorders, such as multiple sclerosis and ALS; other neuropathies and neuralgia; multiple sclerosis; amyotropical lateral sclerosis; stroke and head trauma.

In particular, the compounds according to the invention are also useful in the treatment or prevention of addiction disorders, including but not limited to substance dependence or abuse with or without physiological dependence, particularly where the substance is alcohol, amphetamines, amphetamine-like substances, caffeine, cocaine, hallucinogens, inhalants, nicotine, opioids (such as cannabis, heroin and morphine), phencyclidine, phencyclidine-like compounds, sedative-hypnotics, benzodiazepines and/or other substances, particularly useful for treating withdrawal from the above substances and alcohol withdrawal delirium.

In particular, the compounds according to the invention are also useful in the treatment or prevention of mood disorders induced particularly by alcohol, amphetamines, caffeine, cannabis, cocaine, hallucinogens, inhalants, nicotine, opioids, phencyclidine, sedatives, hypnotics, anxiolytics and other substances.

In particular, the compounds according to the invention are also useful in the treatment or prevention of sexual dysfunction, including but not limited to sexual desire disorders; sexual arousal disorders; orgasmic disorders; sexual pain disorders; sexual dysfunction due to a general medical condition; substance-induced sexual dysfunction and sexual dysfunction not otherwise specified.

In particular, the compounds according to the invention are also useful in the treatment or prevention of pain, including but not limited to traumatic pain such as postoperative pain; traumatic avulsion pain such as brachial plexus; chronic pain such as arthritic pain such as occurring in osteo-rheumatoid or psoriatic arthritis; neuropathic pain such as post-herpetic neuralgia, trigeminal neuralgia, segmental or intercostal neuralgia, fibromyalgia, causalgia, peripheral neuropathy, diabetic neuropathy, chemotherapy-induced neuropathy, AIDS related neuropathy, occipital neuralgia, geniculate neuralgia, glossopharyngeal neuralgia, reflex sympathetic dystrophy and phantom limb pain; various forms of headache such as migraine, acute or chronic tension headache, temporomandibular pain, maxillary sinus pain and cluster headache; odontalgia; cancer pain; visceral pain; gastrointestinal pain; nerve entrapment pain; sport's injury pain; dysmennorrhoea; menstrual pain; meningitis; arachnoiditis; musculoskeletal pain; low back pain such as spinal stenosis, prolapsed disc, sciatica, angina, ankylosing spondyolitis; gout; burns; scar pain; itch; and thalamic pain such as post stroke thalamic pain.

In particular, the compounds according to the invention are also useful in the treatment or prevention of the following other CNS-related conditions: akinesia, akinetic-rigid syndromes, dyskinesia and medication-induced parkinsonism, Gilles de la Tourette syndrome and its symptoms, tremor, chorea, myoclonus, tics and dystonia, attention-deficit/hyperactivity disorder (ADHD), Parkinson's disease, drug-induced Parkinsonism, post-encephalitic Parkinsonism, progressive supranuclear palsy, multiple system atrophy, corticobasal degeneration, parkinsonism-ALS dementia complex and basal ganglia calcification, behavioral disturbances and conduct disorders in dementia and the mentally retarded, including restlessness and agitation, extra-pyramidal movement disorders, Down's syndrome and Akathisia.

In particular, the compounds according to the invention are also useful in the treatment or prevention of inflammation, including but not limited to inflammatory conditions in asthma, influenza, chronic bronchitis and rheumatoid arthritis; inflammatory conditions in the gastrointestinal tract such as, but not limited to Crohn's disease, ulcerative colitis, inflammatory bowel disease and non-steroidal anti-inflammatory drug induced damage; inflammatory conditions of the skin such as herpes and eczema; inflammatory conditions of the bladder such as cystitis and urge incontinence; eye and dental inflammation and pancreatitis, in particular chronic and acute pancreatitis.

In particular, the compounds according to the invention are also useful in the treatment or prevention of allergic disorders, including but not limited to allergic disorders of the skin such as but not limited to urticaria; and allergic disorders of the airways such as but not limited to rhinitis.

In particular, the compounds according to the invention are also useful in the treatment or prevention of emesis, i.e. nausea, retching and vomiting, including but not limited to acute emesis, delayed emesis and anticipatory emesis; emesis induced by drugs such as cancer chemotherapeutic agents such as alkylating agents, for example cyclophosphamide, carmustine, lomustine and chlorambucil; cytotoxic antibiotics, for example dactinomycin, doxorubicin, mitomycin-C and bleomycin; anti-metabolites, for example cytarabine, methotrexate and 5-fluorouracil; vinca alkaloids, for example etoposide, vinblastine and vincristine; and other drugs such as cisplatin, dacarbazine, procarbazine and hydroxyurea; and combinations thereof; radiation sickness; radiation therapy, such as in the treatment of cancer; poisons; toxins such as toxins caused by metabolic disorders or by infection, such as gastritis, or released during bacterial or viral gastrointestinal infection; pregnancy; vestibular disorders, such as motion sickness, vertigo, dizziness and Meniere's disease; post-operative sickness; gastrointestinal obstruction; reduced gastrointestinal motility; visceral pain, such as myocardial infarction or peritonitis; migraine; increased intracranial pressure; decreased intracranial pressure (such as altitude sickness); opioid analgesics, such as morphine; gastro-oesophageal reflux disease; acid indigestion; over-indulgence of food or drink; acid stomach; sour stomach; waterbrash/regurgitation; heartburn, such as episodic heartburn, nocturnal heartburn and meal induced heartburn; and dyspepsia.

In particular, the compounds according to the invention are also useful in the treatment or prevention of gastrointestinal disorders, including but not limited to irritable bowel syndrome (IBS), skin disorders such as psoriasis, pruritis and sunburn; vasospastic diseases such as angina, vascular headache and Reynaud's disease, cerebral ischaemia such as cerebral vasospasm following subarachnoid haemorrhage; fibrosing and collagen diseases such as scleroderma and eosinophilic fascioliasis; disorders related to immune enhancement or suppression such as systemic lupus erythematosus and rheumatic diseases such as fibrositis; cough; and body weight control, including obesity.

Most in particular, the compound according to the invention are useful for the manufacture of a medicament for the treatment and/or prophylaxis of schizophrenia, emesis, anxiety and depression, irritable bowel syndrome (IBS), circadian rhythm disturbances, pre-eclampsia, nociception, pain, in particular visceral and neuropathic pain, pancreatitis, neurogenic inflammation, asthma, chronic obstructive pulmonary disease (COPD) and micturition disorders such as urinary incontinence.

The present invention also relates to a method for the treatment and/or prophylaxis of schizophrenia, emesis, anxiety and depression, irritable bowel syndrome (IBS), circadian rhythm disturbances, pre-eclampsia, nociception, pain, in particular visceral and neuropathic pain, pancreatitis, neurogenic inflammation, asthma, chronic obstructive pulmonary disease (COPD) and micturition disorders such as urinary incontinence comprising administering to a human in need of such administration an effective amount of a compound according to the invention, in particular according to Formula (I), the pharmaceutically acceptable acid or base addition salts thereof, the stereochemically isomeric forms thereof, the N-oxide form thereof, as well as the pro-drugs thereof.

The invention also relates to a pharmaceutical composition comprising a pharmaceutically acceptable carrier and, as active ingredient, a therapeutically effective amount of a compound according to the invention, in particular a compound according to Formula (I), the pharmaceutically acceptable acid or base addition salts thereof, the stereochemically isomeric forms thereof, the N-oxide form thereof and a pro-drug thereof.

The compounds according to the invention, in particular the compounds according to Formula (I), the pharmaceutically acceptable acid or base addition salts thereof, the stereochemically isomeric forms thereof, the N-oxide form thereof and the prodrugs thereof, or any subgroup or combination thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Since the compounds according to the invention are potent orally, mainly centrally active NK-antagonists, pharmaceutical compositions comprising said compounds for administration orally are especially advantageous.

Synthesis

The compounds according to the invention can generally be prepared by a succession of steps, each of which is known to the skilled person.

The final compounds of Formula (Ia) are conveniently prepared by reacting an intermediate compound of Formula (IIa) with 1,1'-carbonyldiimidazole. The reaction may be performed in an inert solvent such as, for example, dichloromethane. The reaction may conveniently be carried out at room temperature.

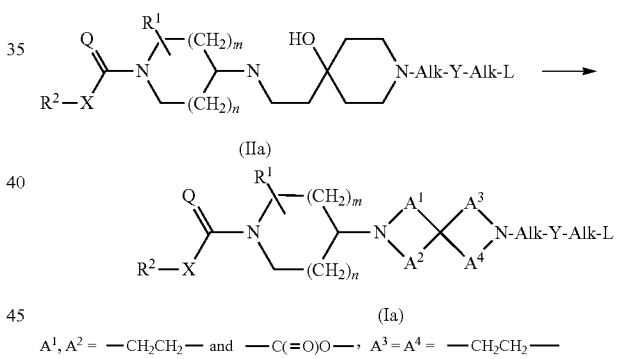

The final compounds of Formula (Ib) can be prepared by reductively N-alkylating an intermediate compound of Formula (IIb) with an intermediate compound of Formula (III). Said reductive N-alkylation may be performed in a reaction-inert solvent such as, for example, dichloromethane, ethanol or toluene or a mixture thereof, and in the presence of an appropriate reducing agent such as, for example, a borohydride, e.g. sodium borohydride, sodium cyanoborohydride or triacetoxy borohydride. In case a borohydride is used as a reducing agent, it may be convenient to use a complex-forming agent such as, for example, titanium(IV) isopropylate as described in J. Org. Chem, 1990, 55, 2552-2554. It may also be convenient to use hydrogen as a reducing agent in combination with a suitable catalyst such as, for example, palladium-on-charcoal or platinum-on-charcoal. In case hydrogen is used as reducing agent, it may be advantageous to add a dehydrating agent to the reaction mixture such as, for example, aluminium tert-butoxide. In order to prevent the undesired further hydro-genation of certain functional groups in the reactants and the reaction products, it may also be advantageous to add an appropriate catalyst-poison to the reaction mixture, e.g., thiophene or quinoline-sulphur. Stirring and optionally elevated temperatures and/or pressure may enhance the rate of the reaction.

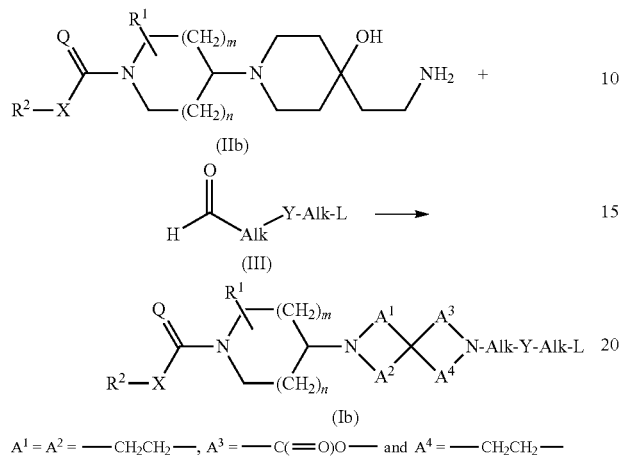

(IIb)

(III)

(Ib)

$A^1 = A^2 = —CH_2CH_2—$, $A^3 = —C(=O)O—$ and $A^4 = —CH_2CH_2—$

Especially advantageous is the preparation of a final compound in which the Alk-Y-Alk-L-moiety is benzyl. Said final compound is pharmacologically active and can be converted into a final compound according to Formula (I') in which the Alk-Y-Alk-L-moiety is hydrogen by reductive hydrogenation using e.g. hydrogen as a reducing agent in combination with a suitable catalyst such as, for example, palladium-on-charcoal or platinum-on-charcoal. The resulting final compound according to the invention can then be converted into other compounds according to Formula (I) by art-known transformations, e.g. acylation and alkylation.

(Ia)

(I')

$A^1, A^2 = —CH_2CH_2—$ and $—C(=O)O—$, $A^3 = A^4 = —CH_2CH_2—$

In particular, the final compounds of Formula (Ic) can be prepared by reacting a final compound of Formula (I') with an intermediate compound of Formula (IV) wherein $W^1$ is an appropriate leaving group such as, for example, a halogen, e.g. chloro or bromo, or a sulfonyloxy leaving group, e.g. methanesulfonyloxy or benzenesulfonyloxy. The reaction can be performed in a reaction-inert solvent such as, for example, a chlorinated hydrocarbon, e.g. dichloromethane or a ketone, e.g. methyl isobutylketone, and in the presence of a suitable base such as, for example, sodium carbonate, sodium hydrogen carbonate or triethylamine. Stirring may enhance the rate of the reaction. The reaction may conveniently be carried out at a temperature ranging between room temperature and reflux temperature.

(I')

(IV)

(Ic)

Alternatively, the final compounds of Formula (Id) can also be prepared by reacting a final compound of Formula (I') with a carboxylic acid of Formula (V). The reaction can be performed in a reaction-inert solvent such as, for example, a chlorinated hydrocarbon, e.g. dichloromethane, in the presence of a suitable base such as, for example, sodium carbonate, sodium hydrogen carbonate or triethylamine and in the presence of an activator, such as e.g. DCC (dicyclohexylcarbodiimide), CDI (carbonyl-diimidazole) and EDCI. Stirring may enhance the rate of the reaction. The reaction may conveniently be carried out at a temperature ranging between room temperature and reflux temperature.

(I')

(V)

(Id)

The final compounds of Formula (Ie) can be prepared by alkylation of a final compound of Formula (I') with compound of Formula (VI) wherein $W^2$ in Formula (VI) is an appropriate leaving group such as, for example, a halogen, e.g. chloro or bromo, or a sulfonyloxy leaving group, e.g. methanesulfonyloxy or benzenesulfonyl-oxy. The reaction can be performed in a reaction-inert solvent such as, for example, a chlorinated hydrocarbon, e.g. dichloromethane, an alcohol, e.g. ethanol, or a ketone, e.g. methyl isobutylketone, and in the presence of a suitable base such as, for example, sodium carbonate, sodium hydrogen carbonate or triethylamine. Stirring may enhance the rate of the reaction. The reaction may conveniently be carried out at a temperature ranging between room temperature and reflux temperature.

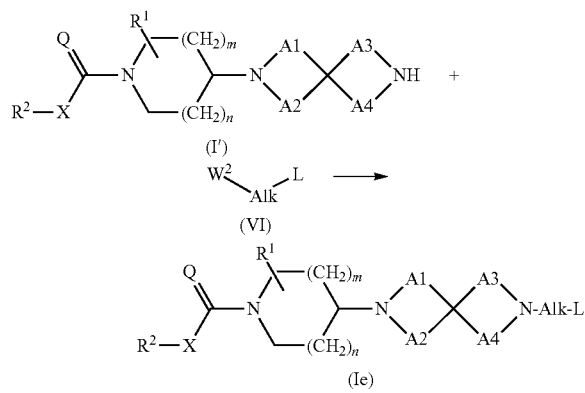

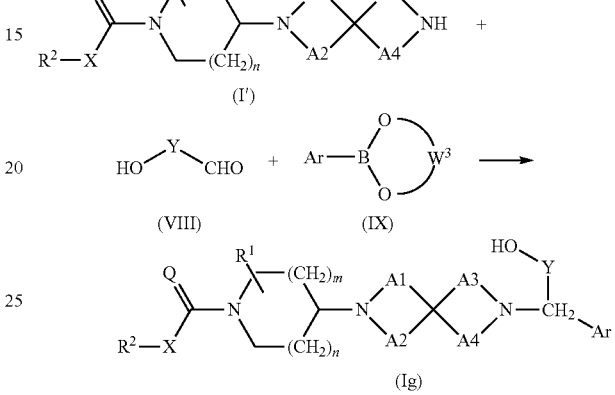

The final compounds of Formula (If) can be prepared by reductively N-alkylating an intermediate compound of Formula (I') with an intermediate compound of Formula (VII). Said reductive N-alkylation may be performed in a reaction-inert solvent such as, for example, dichloromethane, ethanol or toluene or a mixture thereof, and in the presence of an appropriate reducing agent such as, for example, a borohydride, e.g. sodium borohydride, sodium cyanoborohydride or triacetoxy borohydride. In case a borohydride is used as a reducing agent, it may be convenient to use a complex-forming agent such as, for example, titanium(IV) isopropylate as described in J. Org. Chem., 1990, 55, 2552-2554. It may also be convenient to use hydrogen as a reducing agent in combination with a suitable catalyst such as, for example, palladium-on-charcoal or platinum-on-charcoal. In case hydrogen is used as reducing agent, it may be advantageous to add a dehydrating agent to the reaction mixture such as, for example, aluminium tert-butoxide. In order to prevent the undesired further hydrogenation of certain functional groups in the reactants and the reaction products, it may also be advantageous to add an appropriate catalyst-poison to the reaction mixture, e.g., thiophene or quinoline-sulphur. Stirring and optionally elevated temperatures and/or pressure may enhance the rate of the reaction.

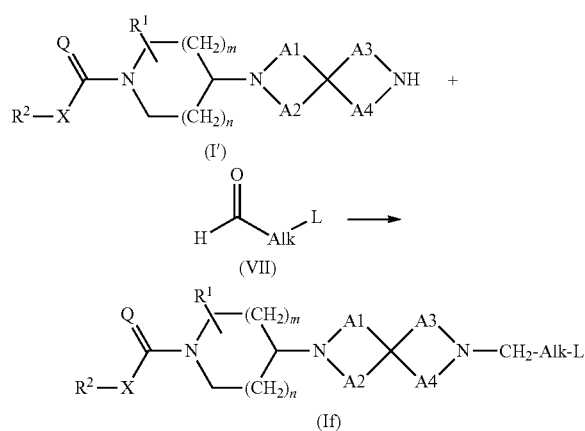

The final compounds of formula (Ig) are conveniently prepared by a Boronic Mannich reaction as described in Tetrahedron, 1997, 53, 16463-16470; J. Am. Chem. Soc. 1998, 120, 11798-11799 or Tetrahedron Letters, 2002, 43, 5965-5968 with an intermediate compound of Formula (I') and intermediate compounds (VIII) and (IX) wherein Y in formula (VIII) is a bivalent radical of formula —CH$_2$— or >C(=O) and W$^3$ in Formula (IX) is hydrogen or an alkyl chain. Said Boronic Mannich reaction may be reacted in the manner of a one-pot reaction with a carbohydrate or its dimer of Formula (VIII) and an arylboronic acid or arylboronic ester of Formula (IX) in a reaction-inert solvent such as, for example, dichlomethane, ethanol, or 2,2,2-trifluoroethanol or a mixture thereof. Stirring may enhance the rate of the reaction. The reaction may conveniently be carried out at a temperature ranging between room temperature and reflux temperature.

The following examples are intended to illustrate but not to limit the scope of the present invention.

Experimental Part

Hereinafter "RT" means room temperature, "CDI" means 1,1'-carbonyldiimidazole, "DIPE" means diisopropylether, "MIK" means methyl isobutyl keton, "BINAP" means[1,1'-binaphthalene]-2,2'-diylbis[diphenylphosphine], "NMP" means 1-methyl-2-pyrrolidinone, "Pd$_2$(dba)$_3$" means tris(dibenzylideneacetone)dipalladium, "DMF" means N,N-dimethylformamide, "EDCI" means 1-ethyl-3-(3-dimethylamino-propyl)carbodiimide hydrochloride and "HOBT" means hydroxybenzotriazole.

PREPARATION OF THE INTERMEDIATE COMPOUNDS

Example A1 a. Preparation of Intermediate Compound 1

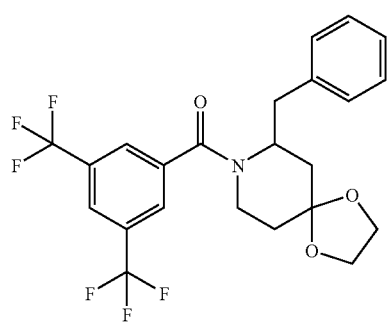

Et₃N (0.55 mol) was added to a stirring mixture of 7-(phenylmethyl)-1,4-dioxa-8-azaspiro[4.5]decane (0.5 mol) in toluene (1500 ml). 3,5-Bis(trifluoromethyl)benzoyl chloride (0.5 mol) was added over a 1-hour period (exothermic reaction). The mixture was stirred at room temperature for 2 hours, then allowed to stand for the weekend and washed three times with water (500 ml, 2×250 ml). The organic layer was separated, dried, filtered and the solvent was evaporated. Yield: 245 g (100%). Crystallization of 2 gram of this fraction from petroleum ether yielded 1 g of intermediate compound 1. (50%).

b. Preparation of Intermediate Compound 2

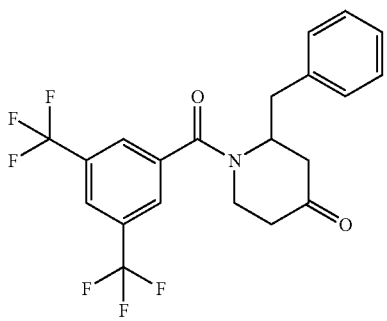

HCl cp (300 ml) was added to a mixture of intermediate compound 1 (0.5 mol) in ethanol (300 ml) and H₂O (300 ml). The reaction mixture was stirred at 60° C. for 20 hours. The precipitate was filtered off, ground, stirred in H₂O, filtered off, washed with petroleum ether and dried. Yield: 192 g of intermediate compound 2 ((±)-1-[3,5-bis(trifluoromethyl)benzoyl]-2-(phenylmethyl)-4-piperidinone) (89.4%) (miture of R and S enantiomers).

c. Preparation of Intermediate Compound 3 and Intermediate Compound 4

(3)

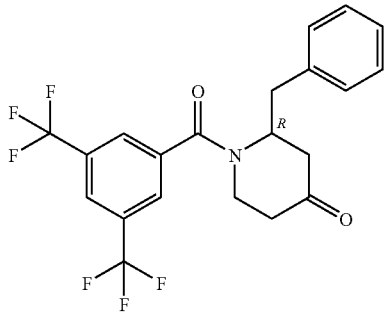

-continued (4)

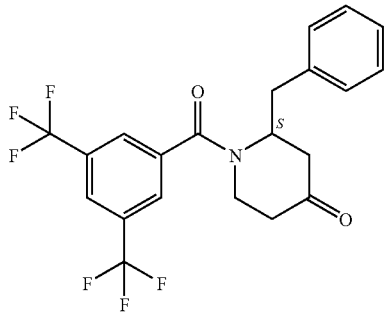

Intermediate compound 2 was separated into its optical isomers by chiral column chromatography over Chiralpak (CHIRALPAK AS 1000 Å 20 mm (DAICEL); eluent: hexane/2-propanol 70/30). Two product fractions were collected and each solvent was evaporated. Yield Fraction 1: 32.6 g of intermediate compound 3 (R), and Fraction 2: 30.4 g of intermediate compound 4 (S).

Example A2 a. Preparation of Intermediate Compound 5 and Intermediate Compound 11 intermediate 5

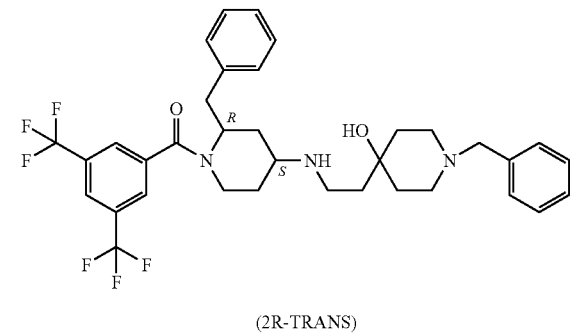

(2R-TRANS)

intermediate 11

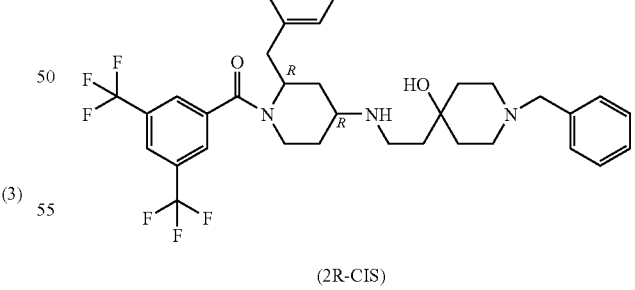

(2R-CIS)

A mixture of 4-(2-aminoethyl)-1-(phenylmethyl)-4-piperidinol (prepared according to the teachings in *European Journal of Medicinal Chemistry* (1974), 9(4), 416-23 of which the content is included herein by reference) (0.0723 mol), intermediate compound 2 (prepared according to A1.b) (0.082 mol) and Pd/C (3.57 g) in Ti(iPrO)₄ (39 ml), CH₃OH (370 ml) and thiophene (2.5 ml) was hydrogenated at 50° C. for 30 hours under a 3 bar pressure, then filtered over celite.

Celite was washed with CH₃OH/CH₂Cl₂. The filtrate was evaporated. The residue was dissolved in CH₂Cl₂, poured out into H₂O, basified with K₂CO₃ 10% and H₂O, stirred for 10 minutes and filtered over celite. Celite was washed with CH₂Cl₂ several times. The filtrate was extracted with CH₂Cl₂. The organic layer was washed with CH₂Cl₂, dried (MgSO₄), filtered and the solvent was evaporated till dryness. The residue was purified by column chromatography over Kromasil (eluent: CH₂Cl₂/CH₃OH/NH₄OH 90/10/0.1 to 90/10/0.4; 20-45 μm). The pure fractions were collected and the solvent was evaporated. Yield Fraction 1: 3.8 g of intermediate compound 5 (2R-TRANS) (8%), and Fraction 2: 7.3 g of intermediate compound 11 (2R-CIS) (16%).

b. Preparation of Intermediate Compound 12

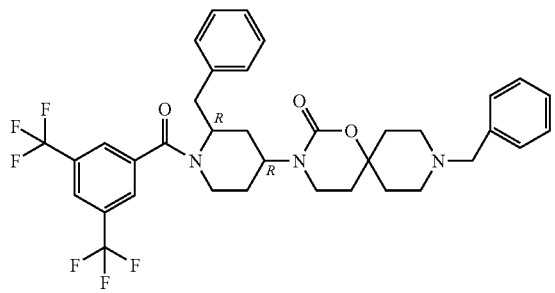

(2R-CIS)

N-ethyl-N-(1-methylethyl)-2-propanamine (0.0059 mol) and then triphosgene (0.0014 mol) were added at 0° C. to a solution of intermediate 11 (prepared according to A2.a) (0.0029 mol) in CH₂Cl₂ (100 ml). The mixture was stirred for 2 hours. H₂O and ice were added. The organic layer was washed with NaCl, dried (MgSO₄), filtered and the solvent was evaporated till dryness. The residue (1.2 g) was purified by column chromatography over silica gel (eluent: CH₂Cl₂/CH₃OH/NH₄OH 97/3/0.1; 15-40 μm). The pure fractions were collected and the solvent was evaporated. Yield: 0.62 g of intermediate compound 12 (2R-CIS) (30%).

c. Preparation of Intermediate Compound 13

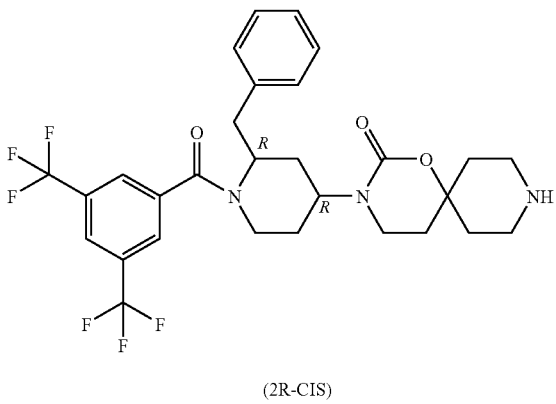

(2R-CIS)

A mixture of intermediate compound 12 (prepared according to A2.b) (0.0009 mol) and Pd/C 10% (0.1 g) in CH₃OH (15 ml) was hydrogenated at room temperature for 18 hours under a 3 bar pressure, then filtered over celite. Celite was washed with CH₂Cl₂/CH₃OH. The filtrate was evaporated. Yield: 0.46 g of intermediate compound 13 (86%).

Example A3 a. Preparation of Intermediate Compound 6 and 7

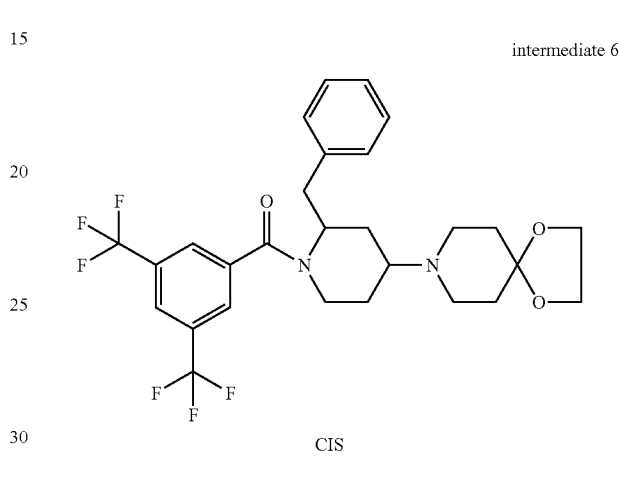

CIS

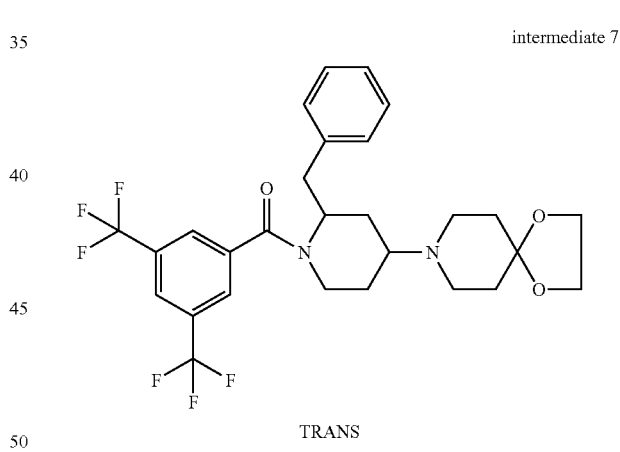

TRANS

A mixture of intermediate compound 2 (prepared according to A1.b) (0.1 mol), 1,4-dioxa-8-azaspiro[4.5]decane (0.1 mol) and Ti(iPrO)₄ (0.1 mol) in CH₃OH (500 ml) was hydrogenated at 50° C. under H₂ with Pd/C 10% (5 g) as a catalyst in the presence of thiophene solution (3 ml). After uptake of H₂ (1 equivalent), the catalyst was filtered off and the filtrate was evaporated. The residue was taken up in CH₂Cl₂/H₂O and stirred for 15 minutes. The organic layer was separated, washed with H₂O, dried and the solvent was evaporated. The residue was purified by column chromatography over silica gel (eluent gradient: CH₂Cl₂/CH₃OH 98/2, 97/3). Two product fractions were collected and their solvent was evaporated. Yield Fraction 1: 17 g (impure). Yield Fraction 2: 12.7 g of intermediate compound 6. Yield Fraction 3: 13.7 g of intermediate compound 7.

b. Preparation of Intermediate Compound 8

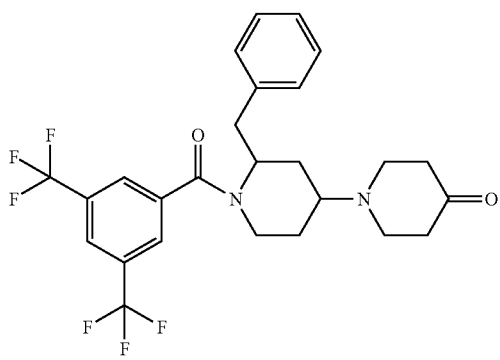

A mixture of intermediate compound 7 (prepared according to A3.a) (0.025 mol) in HCl (concentrated) (200 ml) was stirred for 4 hours at room temperature. The reaction mixture was poured out into ice/(50% NaOH solution) and $CH_2Cl_2$ was added. The organic layer was separated, washed 2 times with $H_2O$, dried and the solvent was evaporated. Toluene was added to the residue and the solvent was evaporated. Then, the residue was crystallised from DIPE. Yield: 10.85 g of intermediate compound 8.

c. Preparation of Intermediate Compound 9

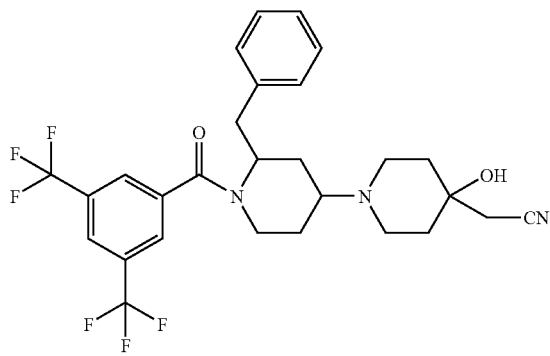

nBuLi 1.6M (0.012 mol) was added slowly at −20° C. to a solution of isopropylamine (0.012 mol) in THF (20 ml). The mixture was cooled to −70° C. A solution of acetonitrile (0.012 mol) in THF (10 ml) was added slowly. The mixture was stirred at −70° C. for 1 hour. Intermediate compound 8 (prepared according to A3.b) (0.006 mol) in THF (40 ml) was added slowly. The mixture was stirred at −78° C. for 30 minutes, poured out into saturated $NH_4Cl$ and extracted with EtOAc. The organic layer was separated, dried ($MgSO_4$), filtered, and the solvent was evaporated. The residue (2.2 g) was purified by column chromatography over silica gel (eluent: $CH_2Cl_2/CH_3OH/NH_4OH$ 95/5/0.1; 15-40 μm). The pure fractions were collected and the solvent was evaporated. Yield: 1.2 g of intermediate compound 9 (34%).

d. Preparation of Intermediate Compound 10

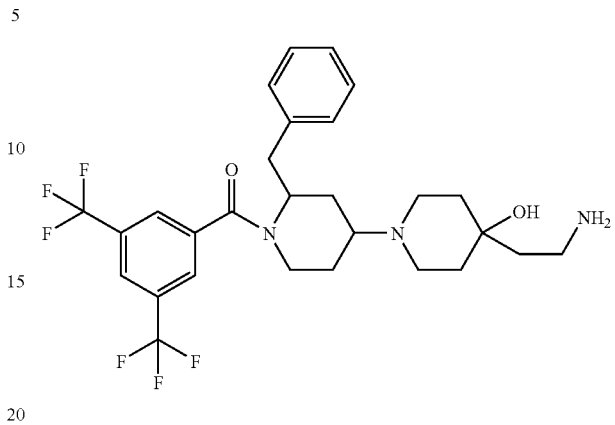

A mixture of intermediate compound 9 (prepared according to A3.c) (0.002 mol) and NiRa (1.2 g) in MeOH/$NH_3$ (20 ml) was hydrogenated at room temperature for 2 hours under a 3 bar pressure, then filtered over celite. Celite was washed with $CH_2Cl_2/CH_3OH$. The filtrate was evaporated. The organic layer was separated, dried ($MgSO_4$), filtered, and the solvent was evaporated. Yield: 1 g of intermediate compound 10 (82%).

Preparation of the Final Compounds

Example B1 a. Preparation of Final Compound 1.2

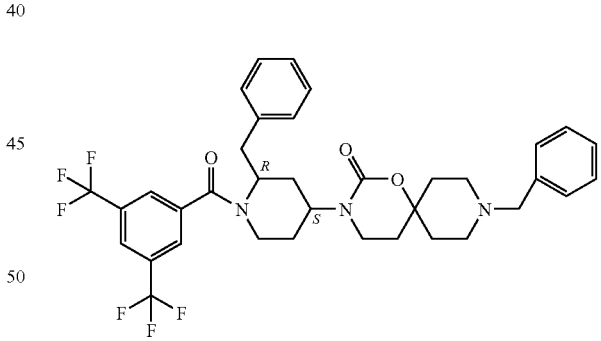

(2R-TRANS)

CDI (0.004 mol) was added portionwise at room temperature to a solution of intermediate compound 5 (prepared according to A2) (0.003 mol) in $CH_2Cl_2$ (20 ml). The mixture was stirred at room temperature for 18 hours. The organic layer was washed with $K_2CO_3$ 10%, dried ($MgSO_4$), filtered, and the solvent was evaporated. The residue (1.9 g) was purified by column chromatography over silica gel (eluent: $CH_2Cl_2/CH_3OH/NH_4OH$ 97/3/0.1; 15-40 μm). The pure fractions were collected and the solvent was evaporated. Yield: 0.58 g of final compound 1.2 (32%).

b. Preparation of Final Compound 1.1

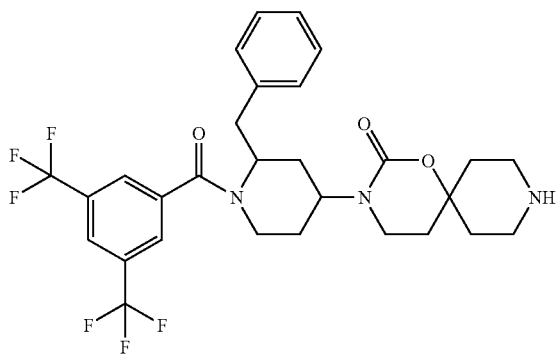

A mixture of final compound 1.2 (0.001 mol) and Pd/C (0.5 g) in CH₃OH (6 ml) was hydrogenated at 50° C. for 18 hours under 3 bar pressure, then filtered over celite. Celite was washed with CH₂Cl₂/CH₃OH. The filtrate was evaporated. Yield: 0.57 g of final compound 1.1 (100%).

Example B2

Preparation of Final Compound 1.4

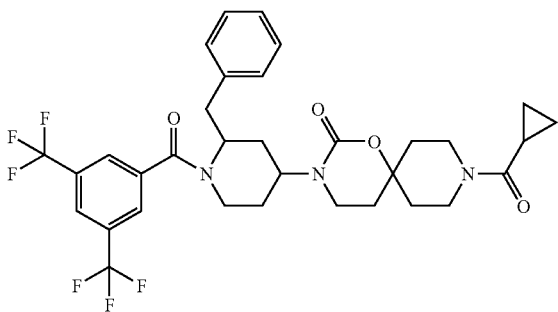

EDCI (0.001 mol) was added portionwise at room temperature to a solution of final compound 1.1 (0.001 mol), cyclopropanecarboxylic acid (0.001 mol), HOBt (0.001 mol) and Et₃N (0.001 mol) in CH₂Cl₂ (6 ml). The mixture was stirred at room temperature for 18 hours. The organic layer was washed with K₂CO₃ 10%, dried (MgSO₄), filtered, and the solvent was evaporated. The residue (0.6 g) was purified by column chromatography over silica gel (eluent gradient: CH₂Cl₂/CH₃OH 98/2 to 95/5; 45-60 μm). The pure fractions were collected and the solvent was evaporated. Yield: 0.55 g of final compound 1.4. When the L-moiety should contain a chiral center, the mixture may either be further separated using appropriate column chromatography or chiral chemicals can be used for preparation (e.g. final compound 1.6 using (3R)-tetrahydro-3-furan carboxylic acid, which is commercially available).

Example B3

Preparation of Final Compound 2.24

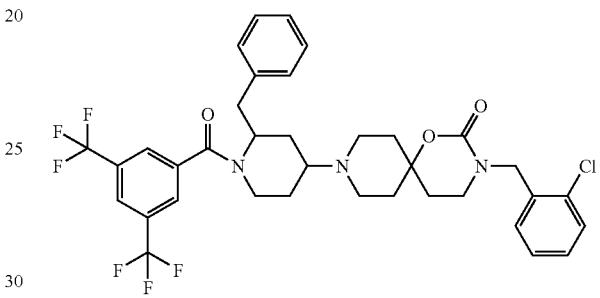

o-Chlorobenzaldehyde (1.2 equivalents) was added at room temperature to a solution of intermediate compound 10 (prepared according to A3.d) in MeOH. The mixture was stirred at room temperature for 1 hour. NaBH₃CN (1.2 equivalents) was added. The mixture was stirred at room temperature for 18 hours, filtered and washed with CH₂Cl₂. PS-TS-NHNH₂ (0.6 equivalents) was added. The mixture was stirred at room temperature for 3 hours. Yield: 11 mg (4.3%) of final compound 2.24.

The following compounds were made according to one of the examples above.

TABLE 1

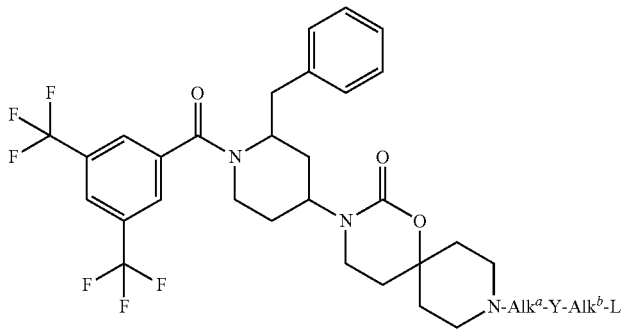

| Comp. No. | Exp. No. | Alk$^a$ | Y | Alk$^b$ | L | stereo descriptors |
|---|---|---|---|---|---|---|
| 1.1 | B1.b | cb | cb | cb | H | 2R-trans |
| 1.2 | B1.a | —CH₂— | cb | cb | 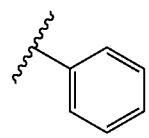 | 2R-trans |

TABLE 1-continued
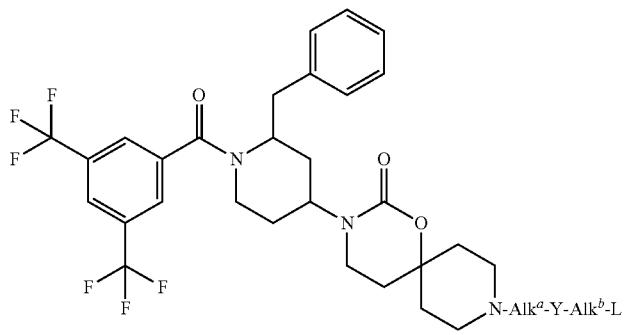
| Comp. No. | Exp. No. | Alk$^a$ | Y | Alk$^b$ | L | stereo descriptors |
|---|---|---|---|---|---|---|
| 1.3 | B2 | cb | C=O | cb | 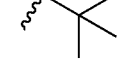 | 2R-trans |
| 1.4 | B2 | cb | C=O | cb |  | 2R-trans |
| 1.5 | B2 | cb | C=O | cb | 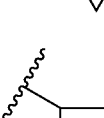 | 2R-trans |
| 1.6 | B2 | cb | C=O | cb | 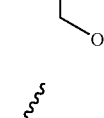 | 2R-cis |
| 1.7 | B2 | cb | C=O | cb | 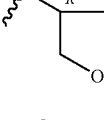 | 2R-trans |
| 1.8 | B2 | cb | C=O | cb | 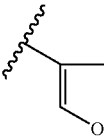 | 2R-cis |
| 1.9 | B2 | cb | C=O | cb | 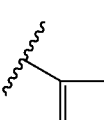 | 2R-trans |
| 1.10 | B2 | cb | C=O | cb | 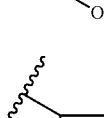 | 2R-trans |

TABLE 1-continued
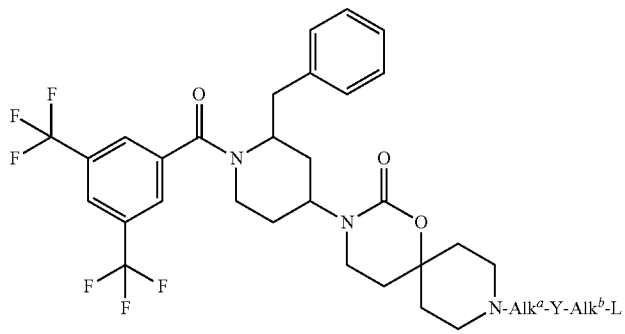
| Comp. No. | Exp. No. | Alk$^a$ | Y | Alk$^b$ | L | stereo descriptors |
|---|---|---|---|---|---|---|
| 1.11 | B2 | cb | C=O | cb | phenyl | 2R-trans |
| 1.12 | B2 | cb | C=O | cb | phenyl | 2R-cis |
| 1.13 | B2 | cb | C=O | cb | pyrazinyl | 2R-trans |
cb: covalent bond
TABLE 2
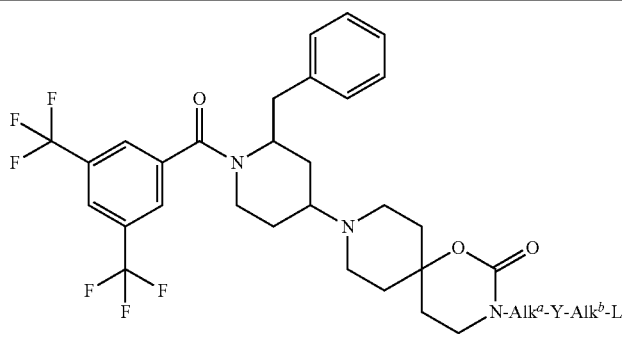
| Comp. No. | Exp. No. | Alk$^a$ | Y | Alk$^b$ | L | stereo descriptors |
|---|---|---|---|---|---|---|
| 2.1 | B3 | —CH$_2$— | cb | cb | t-Bu | 2R-cis |
| 2.2 | B3 | —CH$_2$— | cb | cb | t-Bu | 2R-trans |

TABLE 2-continued
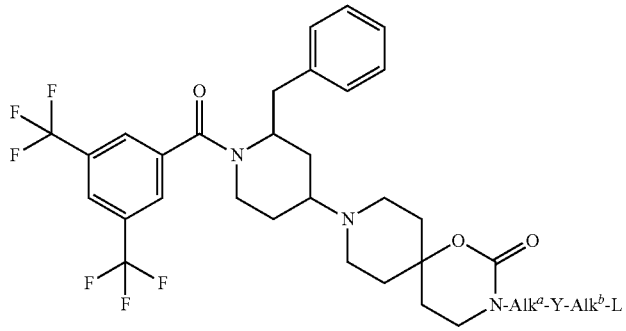
| Comp. No. | Exp. No. | Alk$^a$ | Y | Alk$^b$ | L | stereo descriptors |
|---|---|---|---|---|---|---|
| 2.3 | B3 | —CH$_2$— | cb | cb | 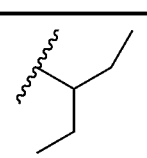 | 2R-cis |
| 2.4 | B3 | —CH$_2$— | cb | cb | 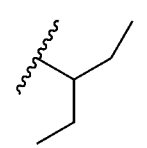 | 2R-trans |
| 2.5 | B3 | —CH$_2$— | cb | cb | 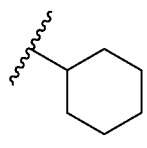 | 2R-trans |
| 2.6 | B3 | —CH$_2$— | cb | cb | 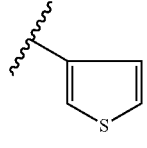 | 2R-cis |
| 2.7 | B3 | —CH$_2$— | cb | cb | 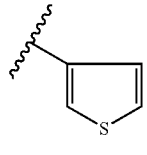 | 2R-trans |
| 2.8 | B3 | —CH$_2$— | cb | cb | 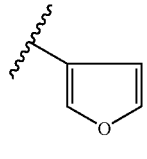 | 2R-cis |
| 2.9 | B3 | —CH$_2$— | cb | cb | 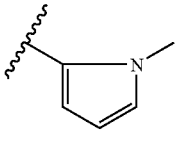 | 2R-cis |
| 2.10 | B3 | —CH$_2$— | cb | cb | 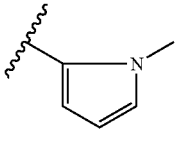 | 2R-trans |

TABLE 2-continued
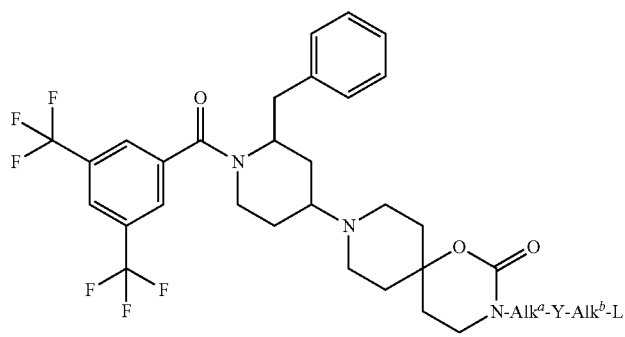
| Comp. No. | Exp. No. | Alk$^a$ | Y | Alk$^b$ | L | stereo descriptors |
|---|---|---|---|---|---|---|
| 2.11 | B3 | —CH$_2$— | cb | cb | 2-methylphenyl | 2R-cis |
| 2.12 | B3 | —CH$_2$— | cb | cb | 2-methylphenyl | 2R-trans |
| 2.13 | B3 | —CH$_2$— | cb | cb | 2-chlorophenyl | 2R-cis |
| 2.14 | B3 | —CH$_2$— | cb | cb | 2-chlorophenyl | 2R-trans |
| 2.15 | B3 | —CH$_2$— | cb | cb | 4-hydroxyphenyl | 2R-cis |
| 2.16 | B3 | —CH$_2$— | cb | cb | pyridin-3-yl | 2R-cis |
| 2.17 | B3 | —CH$_2$— | cb | cb | pyridin-3-yl | 2R-trans |
cb: covalent bond

C. Analytical Data

For all compounds LCMS data were recorded.
LCMS Conditions
General Procedure

The HPLC gradient was supplied by an Alliance HT 2795 (Waters) system consisting of a quaternary pump with degasser, an autosampler, and DAD detector. Flow from the column was split to the MS detector. MS detectors were configured with an electrospray ionization source. The capillary needle voltage was 3 kV and the source temperature was maintained at 100° C. Nitrogen was used as the nebulizer gas. Data acquisition was performed with a Waters-Micromass Mass-Lynx-Openlynx data system.

Method 1:

In addition to the general procedure: Reversed phase HPLC was carried out on a Kromasil C18 column (5 µm, 4.6×150 mm) with a flow rate of 1 ml/min. Two mobile phases (mobile phase A: 100% 6.5 mM ammonium acetate+0.2% formic acid; mobile phase B: 100% acetonitrile) were employed to run a gradient condition from 60% A and 40% B for 1 min. to 100% B in 4 min., 100% B for 5 min to 60% A and 40% B in 3 min., and re-equilibrate with 60% A and 40% B for 3 min. An injection volume of 5 µl was used. Cone voltage was 20 V for positive ionization mode. Mass spectra were acquired by scanning from 100 to 900 in 1 second using a dwell time of 0.1 seconds.

Method 2:

In addition to the general procedure: Reversed phase HPLC was carried out on a Kromasil C18 column (3.5 µm, 4.6×100 mm) with a flow rate of 0.8 ml/min. Three mobile phases (mobile phase A: 100% 7 mM ammonium acetate; mobile phase B: 100% acetonitrile; mobile phase C: 0.2% formic acid+99.8% ultra-pure water) were employed to run a gradient condition from 35% A, 30% B and 35% C (hold for 1 minute) to 100% B in 4 minutes, 100% B for 4 minutes and re-equilibrate with initial conditions for 2 minutes. An injection volume of 10 µl was used. Cone voltage was 20 V for positive and negative ionization mode. Mass spectra were acquired by scanning from 100 to 1000 in 0.4 seconds using an interscan delay of 0.3 seconds.

TABLE 3

LCMS parent peak and retention time for all compounds.

| Comp. no. | LCMS (MH+ or MNH4+) | Retention time (min) | Method | Comment |
|---|---|---|---|---|
| 1.1 | 584 | 4.09 | 1 | |
| 1.2 | 674 | 4.83 | 1 | |
| 1.3 | 668 | 6.36 | 1 | |
| 1.4 | 653 | 5.94 | 1 | |
| 1.5 | 699 | 5.60 | 1 | |
| 1.6 | 682 | 5.85 | 2 | m.p.: 102° C. (Kofler) NMR available |
| 1.7 | 695 | 5.94 | 1 | |
| 1.8 | 678 | 6.04 | 2 | m.p.: 192° C. (Kofler) NMR available |
| 1.9 | 711 | 6.11 | 1 | |
| 1.10 | 727 | 6.03 | 1 | |
| 1.11 | 705 | 6.20 | 1 | |
| 1.12 | 688 | 6.19 | 2 | m.p.: 110° C. (Kofler) NMR available |
| 1.13 | 690 | 5.60 | 1 | |
| 2.1 | 654 | 5.03 | 1 | |
| 2.2 | 654 | 4.93 | 1 | |
| 2.3 | 668 | 5.33 | 1 | |
| 2.4 | 668 | 5.24 | 1 | |
| 2.5 | 680 | 5.23 | 1 | |
| 2.6 | 680 | 4.90 | 1 | |
| 2.7 | 680 | 4.80 | 1 | |
| 2.8 | 664 | 4.70 | 1 | |
| 2.9 | 677 | 4.90 | 1 | |
| 2.10 | 677 | 4.74 | 1 | |
| 2.11 | 688 | 5.20 | 1 | |
| 2.12 | 688 | 5.01 | 1 | |
| 2.13 | 708 | 5.17 | 1 | |
| 2.14 | 708 | 5.10 | 1 | |
| 2.15 | 690 | 4.54 | 1 | |
| 2.16 | 675 | 3.90 | 1 | |
| 2.17 | 675 | 3.73 | 1 | |

D. Pharmacological Example

Example D.1

Binding Experiment for h-$NK_1$, h-$NK_2$ and h-$NK_3$ Receptors

The compounds according to the invention were investigated for interaction with various neurotransmitter receptors, ion channels and transporter binding sites using the radioligand binding technique. Membranes from tissue homogenates or from cells, expressing the receptor or transporter of interests, were incubated with a radioactively labelled substance ([$^3$H]- or [$^{125}$I] ligand) to label a particular receptor. Specific receptor binding of the radioligand was distinguished from the non-specific membrane labelling by selectively inhibiting the receptor labelling with an unlabelled drug (the blank), known to compete with the radioligand for binding to the receptor sites. Following incubation, labelled membranes were harvested and rinsed with excessive cold buffer to remove non-bound radioactivity by rapid filtration under suction. Membrane bound radioactivity was counted in a scintillation counter and results were expressed in counts per minute (cpm).

The compounds were dissolved in DMSO and tested at 10 concentrations ranging from $10^{-10}$ to $10^{-5}$ M.

The ability of the compounds according to the invention to displace [$^3$H]-Substance P from cloned human h-$NK_1$ receptors expressed in CHO cells, to displace [$^3$H]-SR-48968 from cloned human h-$NK_2$ receptors expressed in Sf9 cells, and to displace [$^3$H]-SR-142801 from cloned human h-$NK_3$ receptors expressed in CHO cells was evaluated.

The receptor binding values ($pIC_{50}$) for the h-$NK_1$ ranges for all compounds according to the invention between 10 and 6.

Example D.2

Signal Transduction (ST)

This test evaluates in vitro functional $NK_1$ antagonistic activity. For the measurements of intracellular $Ca^{++}$ concentrations the cells were grown on 96-well (black wall/transparent bottom) plates from Costar for 2 days until they reached confluence. The cells were loaded with 2 µM Fluo3 in DMEM containing 0.1% BSA and 2.5 mM probenecid for 1 h at 37° C. They were washed 3× with a Krebs buffer (140 mM NaCl, 1 mM $MgCl_2 \times 6H_2O$, 5 mM KCl, 10 mM glucose, 5 mM HEPES; 1.25 mM $CaCl_2$; pH 7.4) containing 2.5 mM probenecid and 0.1% BSA ($Ca^{++}$-buffer). The cells were preincubated with a concentration range of antagonists for 20 min at RT and Ca$^{++}$-signals after addition of the agonists were measured in a Fluorescence Image Plate Reader (FLIPR from Molecular Devices, Crawley, England). The peak of the Ca$^{++}$-transient was considered as the relevant signal and the mean values of corresponding wells were analysed as described below.

The sigmoidal dose response curves were analysed by computerised curve-fitting, using the GraphPad Program. The EC$_{50}$-value of a compound is the effective dose showing 50% of maximal effect. For mean curves the response to the agonist with the highest potency was normalised to 100%. For antagonist responses the IC$_{50}$-value was calculated using non-linear regression.

The pIC$_{50}$ data for the signal transduction testing for a representative selection of compounds are presented in Table 4. The last columns indicate—without being limited thereto—for which action the compounds might be most suitable. Of course, since for some neurokinin receptors no data was determined, it is obvious that these compounds might be attributed to another suitable use.

TABLE 4

Pharmacological data for the signal transduction for selected compounds.

| Co. No | NK$_1$ pIC$_{50}$ | NK2 pIC50 | NK3 pIC50 | Suitable for |
|---|---|---|---|---|
| 1.9 | 8.1 | 5.0 | 5.2 | NK$_1$ |
| 1.13 | 7.3 | 5.1 | 5.8 | NK$_1$ |
| 2.1 | 6.6 | <5 | 5.4 | NK$_1$ |
| 2.3 | 6.4 | <5 | 5.3 | NK$_1$ |
| 2.4 | 7.1 | 5.3 | 5.1 | NK$_1$ |
| 2.5 | 6.7 | 5.3 | <5 | NK$_1$ |
| 2.6 | 6.7 | <5 | 5.6 | NK$_1$ |
| 2.7 | 6.8 | 5.4 | 5.0 | NK$_1$ |
| 2.8 | 6.6 | <5 | 5.2 | NK$_1$ |
| 2.9 | 6.2 | 5.0 | 5.5 | NK$_1$ |
| 2.11 | 6.4 | <5 | 5.1 | NK$_1$ |
| 2.12 | 6.6 | 5.4 | 5.3 | NK$_1$ |
| 2.13 | 6.1 | <5 | 5.5 | NK$_1$ |
| 2.14 | 6.4 | 5.2 | 5.1 | NK$_1$ |
| 2.15 | 6.5 | <5 | 5.7 | NK$_1$ |
| 2.16 | 6.4 | <5 | 5.8 | NK$_1$ |
| 2.17 | 7.0 | 5.6 | 5.2 | NK$_1$ |
| 1.8 | 7.6 | n.d. | n.d. | NK$_1$ |
| 1.6 | 7.6 | n.d. | n.d. | NK$_1$ |
| 1.12 | 7.3 | n.d. | n.d. | NK$_1$ |
| 2.2 | 7.2 | 5.7 | 5.4 | NK$_1$/NK$_2$ |
| 2.10 | 7.1 | 5.7 | 5.4 | NK$_1$/NK$_2$ |
| 1.4 | 7.9 | 6.0 | 6.9 | NK$_1$/NK$_2$/NK$_3$ |
| 1.3 | 8.0 | 5.3 | 7.1 | NK$_1$/NK$_3$ |
| 1.5 | 7.9 | 5.1 | 6.6 | NK$_1$/NK$_3$ |
| 1.7 | 7.8 | 5.1 | 6.9 | NK$_1$/NK$_3$ |
| 1.10 | 7.9 | 5.2 | 6.5 | NK$_1$/NK$_3$ |
| 1.11 | 7.5 | <5 | 6.1 | NK$_1$/NK$_3$ |

(n.d. = not determined)

E. Composition Examples

"Active ingredient" (A.I.) as used throughout these examples relates to a compound of Formula (I), the pharmaceutically acceptable acid or base addition salts thereof, the stereochemically isomeric forms thereof, the N-oxide form thereof and prodrugs thereof.

Example E.1

Oral Drops

500 Grams of the A.I. was dissolved in 0.5 l of 2-hydroxypropanoic acid and 1.5 l of the polyethylene glycol at 60–80° C. After cooling to 30–40° C. there were added 35 l of polyethylene glycol and the mixture was stirred well. Then there was added a solution of 1750 grams of sodium saccharin in 2.5 l of purified water and while stirring there were added 2.5 l of cocoa flavor and polyethylene glycol q.s. to a volume of 50 l, providing an oral drop solution comprising 10 mg/ml of A.I. The resulting solution was filled into suitable containers.

Example E.2

Oral Solution

9 Grams of methyl 4-hydroxybenzoate and 1 gram of propyl 4-hydroxybenzoate were dissolved in 4 l of boiling purified water. In 3 l of this solution were dissolved first 10 grams of 2,3-dihydroxybutanedioic acid and thereafter 20 grams of the A.I. The latter solution was combined with the remaining part of the former solution and 12 l 1,2,3-propanetriol and 3 l of sorbitol 70% solution were added thereto. 40 Grams of sodium saccharin were dissolved in 0.5 l of water and 2 ml of raspberry and 2 ml of gooseberry essence were added. The latter solution was combined with the former, water was added q.s. to a volume of 20 l providing an oral solution comprising 5 mg of the active ingredient per teaspoonful (5 ml). The resulting solution was filled in suitable containers.

Example E.3

Film-Coated Tablets

Preparation of Tablet Core

A mixture of 100 grams of the A.I., 570 grams lactose and 200 grams starch was mixed well and thereafter humidified with a solution of 5 grams sodium dodecyl sulfate and 10 grams polyvinylpyrrolidone in about 200 ml of water. The wet powder mixture was sieved, dried and sieved again. Then there was added 100 grams microcrystalline cellulose and 15 grams hydrogenated vegetable oil. The whole was mixed well and compressed into tablets, giving 10.000 tablets, each containing 10 mg of the active ingredient.

Coating

To a solution of 10 grams methyl cellulose in 75 ml of denaturated ethanol there was added a solution of 5 grams of ethyl cellulose in 150 ml of dichloromethane. Then there were added 75 ml of dichloromethane and 2.5 ml 1,2,3-propanetriol. 10 Grams of polyethylene glycol was molten and dissolved in 75 ml of dichloromethane. The latter solution was added to the former and then there were added 2.5 grams of magnesium octadecanoate, 5 grams of polyvinylpyrrolidone and 30 ml of concentrated colour suspension and the whole was homogenated. The tablet cores were coated with the thus obtained mixture in a coating apparatus.

Example E.4

Injectable Solution 1.8 Grams methyl 4-hydroxybenzoate and 0.2 grams propyl 4-hydroxybenzoate were dissolved in about 0.5 l of boiling water for injection. After cooling to about 50° C. there were added while stirring 4 grams lactic acid, 0.05 grams propylene glycol and 4 grams of the A.I. The solution was cooled to room temperature and supplemented with water for injection q.s. ad 1 l, giving a solution comprising 4 mg/ml of A.I. The solution was sterilized by filtration and filled in sterile containers.

The invention claimed is:

1. A compound according to Formula (I)

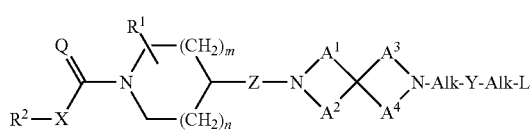

pharmaceutically acceptable acid or base addition salts thereof, stereochemically isomeric forms thereof, N-oxide form thereof, or prodrug thereof, wherein:

$R^2$ is $Ar^2$, $Ar^2$-alkyl, di($Ar^2$)alkyl;

X is a covalent bond or a bivalent radical of formula —O—, —S— or —$NR^3$—;

Q is O or $NR^3$;

each $R^3$ is independently hydrogen or alkyl;

$R^1$ is $Ar^1$, $Ar^1$-alkyl or di($Ar^1$)-alkyl;

n is an integer, equal to 0, 1 or 2;

m is an integer, equal to 1 or 2, provided that if m is 2, then n is 1;

Z is a covalent bond or a bivalent radical of formula —$CH_2$— or >C(=O);

$A^1$, $A^2$, $A^3$ and $A^4$ are each independently $CH_2CH_2$—, —C(=O)O— or —OC(=O)—, provided that at least one of —C(=O)O— or —OC(=O)— is selected and that =O is in an alpha-position relative to the N-atom;

each Alk is independently a covalent bond; a bivalent straight or branched, saturated or unsaturated hydrocarbon radical having from 1 to 6 carbon atoms; or a cyclic saturated or unsaturated hydrocarbon radical having from 3 to 6 carbon atoms; each radical optionally substituted on at least one carbon atom with at least one phenyl, halo, cyano, hydroxy, formyl or amino radical;

Y is a covalent bond or a bivalent radical of formula —C(=O)—, —$SO_2$—, —C(=CH—R)— or —C(=N—R)—, wherein R is H, CN or nitro;

L is hydrogen, alkyl, alkenyl, alkyloxy, alkyloxyalkyloxy, alkylcarbonyloxy, alkyloxycarbonyl, mono- or di(alkyl)amino, mono- or di(alkyloxycarbonyl)amino, mono- or di(alkylcarbonyl)amino, mono- or di($Ar^3$)amino, mono- or di($Ar^3$alkyl)amino, mono- or di($Het^2$)amino, mono- or di($Het^2$alkyl)amino, alkylsulfonyl, norbornyl, adamantyl, tricycloundecyl, $Ar^3$, $Ar^3$-oxy, $Ar^3$-carbonyl, $Het^2$, $Het^2$-oxy, $Het^2$-carbonyl or mono- or di($Het^2$-carbonyl)amino;

$Ar^1$ is phenyl, optionally substituted with 1, 2 or 3 substituents, each independently halo, alkyl, cyano, aminocarbonyl or alkyloxy;

$Ar^2$ is naphthalenyl or phenyl, each optionally substituted with 1, 2 or 3 substituents, each independently halo, nitro, amino, mono- or di(alkyl)amino, cyano, alkyl, hydroxy, alkyloxy, carboxyl, alkyloxycarbonyl, aminocarbonyl or mono- or di(alkyl)aminocarbonyl;

$Ar^3$ is naphthalenyl or phenyl, optionally substituted with 1, 2 or 3 substituents, each independently alkyloxy, alkylcarbonylamino, methanesulfonyl, $Ar^1$carbonyloxyalkyl, $Ar^1$alkyloxycarbonyl, $Ar^1$alkyloxyalkyl, alkyl, halo, hydroxy, pyridinyl, morpholinyl, pyrrolyl, pyrrolidinyl, imidazo[1,2-a]pyridinyl, morpholinylcarbonyl, pyrrolidinylcarbonyl, amino or cyano;

$Het^2$ is a monocyclic heterocyclic radical that is pyrrolidinyl, dihydro-2H-pyranyl, pyranyl, dioxolyl, imidazolidinyl, tetrahydropyridinyl, tetrahydropyrimidinyl, pyrazolidinyl, piperidinyl, morpholinyl, dithianyl, thiomorpholinyl, piperazinyl, imidazolidinyl, tetrahydrofuranyl, 2H-pyrrolyl, pyrrolinyl, imidazolinyl, pyrazolinyl, pyrrolyl, imidazolyl, pyrazolyl, triazolyl, furanyl, thienyl, oxazolyl, dioxazolyl, oxazolidinyl, isoxazolyl, thiazolyl, thiadiazolyl, isothiazolyl, pyridinyl, 1H-pyridinyl, pyrimidinyl, pyrazinyl, pyridazinyl, triazinyl or tetrazolyl; or a bicyclic heterocyclic radical that is 2,3-dihydro-benzo[1,4]dioxine, octahydro-benzo[1,4]dioxine, octabicycloheptyl, benzopiperidinyl, quinolinyl, quinoxalinyl, indolyl, isoindolyl, chromanyl, benzimidazolyl, imidazo[1,2-a]pyridinyl, benzoxazolyl, benzodioxolyl, benzisoxazolyl, benzoxadiazolyl, benzothiazolyl, benzisothiazolyl, benzofuranyl, dihydroisobenzofuranyl, or benzothienyl; wherein each mono-, or bicyclic heterocyclic radical is optionally substituted on any atom with at least one radical that is $Ar^1$, $Ar^1$alkyl, $Ar^1$alkyloxyalkyl, halo, hydroxy, alkyl, piperidinyl, pyrrolyl, thienyl, oxo, alkyloxy, alkylcarbonyl, $Ar^1$carbonyl, mono- or di(alkyl)aminoalkyl, alkyloxyalkyl or alkyloxycarbonyl;

alkyl is a straight or a branched saturated hydrocarbon radical having from 1 to 6 carbon atoms or a cyclic saturated hydrocarbon radical having from 3 to 6 carbon atoms; each hydrocarbon radical optionally substituted on at least one carbon atom with at least one radical that is phenyl, halo, trihalomethyl, aminocarbonyl, methyl, ethyl, propyl, isopropyl, t-butyl, cyano, oxo, hydroxy, formyl or amino; and alkenyl is a straight or branched unsaturated hydrocarbon radical having from 1 to 6 carbon atoms and having at least one unsaturated bond; or a cyclic unsaturated hydrocarbon radical having from 3 to 6 carbon atoms and having at least one unsaturated bond; each hydrocarbon radical optionally substituted on at least one carbon atom with at least one radical that is phenyl, halo, cyano, oxo, hydroxy, formyl or amino.

2. The compound according to claim 1, wherein the spiro-moiety has the Formula (f1) or (f2),

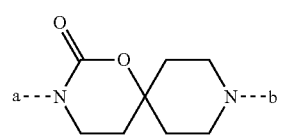

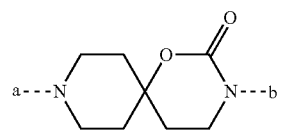

wherein "a" is the piperidinyl-moiety of Formula (I) and "b" is the Alk-Y-Alk-L-moiety of Formula (I).

3. The compound according to claim 1, wherein $R^1$ is benzyl attached to the 2-position or $R^1$ is phenyl attached to the 3-position.

4. The compound according to claim 1, wherein the $R^2$—X—C(=Q)-moiety is 3,5-di-(trifluoromethyl)phenyl-carbonyl.

5. The compound according to claim 1, wherein m and n are both equal to 1.

6. The compound according to claim 1, wherein Z is a covalent bond.

7. The compound according to claim 1, wherein Y is a covalent bond or —C(=O)—.

8. The compound according to claim 1, wherein each Alk is independently a covalent bond or —CH$_2$—.

9. The compound according to claim 1, wherein L is hydrogen, isopropyl, pentyl, cyclopropyl, cyclohexyl, tetrahydrofuranyl, pyrrolyl, furanyl, thienyl, thiadiazolyl, phenyl, pyridinyl or pyrazinyl.

10. The compound according to claim 1, wherein
R$^2$ is phenyl, optionally substituted with 1, 2 or 3 haloalkyl substituents;
X is a covalent bond;
Q is O;
R$^1$ is phenyl or benzyl;
n is an integer, equal to 1;
m is an integer, equal to 1;
Z is a covalent bond;
A$^1$, A$^2$, A$^3$ and A$^4$ are each independently —CH$_2$CH$_2$—, —C(=O)O— or —OC(=O)—, provided that at least one of —C(=O)O— or —OC(=O)— is selected and that =O is in an alpha-position relative to the N-atom;
each Alk is independently a covalent bond or a bivalent, straight, saturated hydrocarbon radical having one or two carbon atoms;
Y is a covalent bond or a bivalent radical of formula —C(=O)—;
L is hydrogen, alkyl, Ar$^3$ or Het$^2$;
Ar$^3$ is phenyl, optionally substituted with a substituent that is alkyl, halo or hydroxy;
Het$^2$ is a monocyclic heterocyclic radical that is tetrahydrofuranyl, pyrrolyl, furanyl, thienyl, thiadiazolyl, pyridinyl, or pyrazinyl; wherein each monocyclic heterocyclic radical is optionally substituted on any atom with at least one-alkyl-radical; and
alkyl is a straight or branched saturated hydrocarbon radical having from 1 to 6 carbon atoms or a cyclic saturated hydrocarbon radicals having from 3 to 6 carbon atoms.

11. The compound according to claim 1 that is:

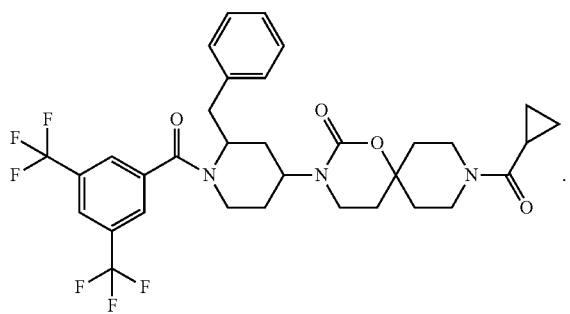

12. A pharmaceutical composition comprising a pharmaceutically acceptable carrier and, as active ingredient, a therapeutically effective amount of a compound according to claim 1.

13. A process of making a pharmaceutical composition according to claim 12, wherein the pharmaceutically acceptable carrier is intimately mixed with a therapeutically effective amount of a compound of Formula (I).

14. A process for preparing a compound according to claim 1, comprising
reacting a compound of Formula (IIa) with 1,1'-carbonyldiimidazole, in a reaction-inert solvent, to obtain a compound according to Formula (Ia),

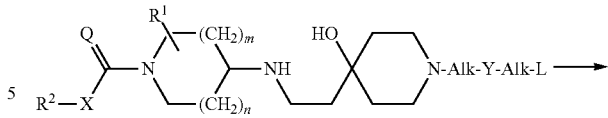

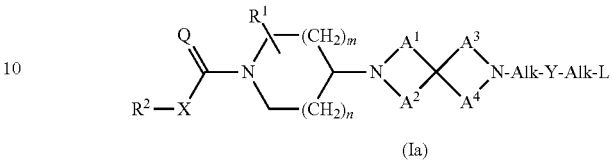

wherein A$^1$ is —CH$_2$CH$_2$—; A$^2$ is —C(=O)O—; and A$^3$ and A$^4$ are each —CH$_2$CH$_2$—; or reductively N-alkylating a compound of Formula (IIb) with a compound of Formula (III), in a reaction-inert solvent and optionally in the presence of a reducing agent, to obtain a compound according to Formula (Ib),

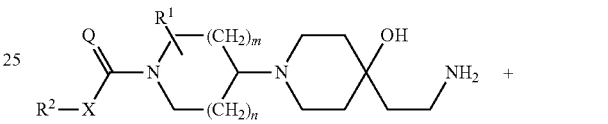

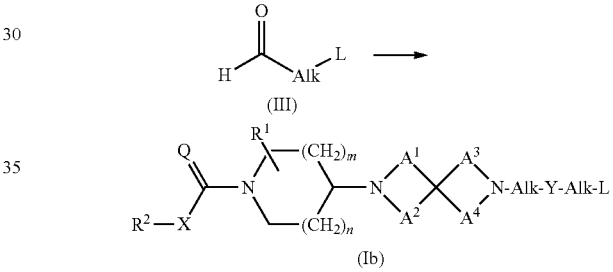

wherein A$^1$ and A$^2$ are —CH$_2$CH$_2$—; A$^3$ is —C(=O)O—; and A$^4$ is —CH$_2$CH$_2$
and further, in the compounds of Formula (Ia), (IIa), (Ib), (IIb) and (III):
R$^2$ is Ar$^2$, Ar$^2$-alkyl, di(Ar$^2$)alkyl;
X is a covalent bond or a bivalent radical of formula —O—, —S— or —NR$^3$—;
Q is O or NR$^3$;
each R$^3$ is independently hydrogen or alkyl;
R$^1$ is Ar$^1$, Ar$^1$-alkyl or di(Ar$^1$)-alkyl;
n is an integer, equal to 0, 1 or 2;
m is an integer, equal to 1 or 2, provided that if m is 2, then n is 1;
Z is a covalent bond or a bivalent radical of formula —CH$_2$— or >C(=O);
each Alk is independently a covalent bond; a bivalent straight or branched, saturated or unsaturated hydrocarbon radical having from 1 to 6 carbon atoms; or a cyclic saturated or unsaturated hydrocarbon radical having from 3 to 6 carbon atoms; each radical optionally substituted on at least one carbon atom with at least one phenyl, halo, cyano, hydroxy, formyl or amino radical;
Y is a covalent bond or a bivalent radical of formula —C(=O)—, —SO$_2$—, —C(=CH—R)— or —C(=N—R)—, wherein R is H, CN or nitro;
L is hydrogen, alkyl, alkenyl, alkyloxy, alkyloxyalkyloxy, alkylcarbonyloxy, alkyloxycarbonyl, mono- or di(alkyl)

amino, mono- or di(alkyloxycarbonyl)amino, mono- or di(alkylcarbonyl)amino, mono- or di($Ar^3$)amino, mono- or di($Ar^3$alkyl)amino, mono- or di($Het^2$)amino, mono- or di($Het^2$alkyl)amino, alkylsulfonyl, norbornyl, adamantyl, tricycloundecyl, $Ar^3$, $Ar^3$-oxy, $Ar^3$-carbonyl, $Het^2$, $Het^2$-oxy, $Het^2$-carbonyl or mono- or di($Het^2$-carbonyl)amino;

$Ar^1$ is phenyl, optionally substituted with 1, 2 or 3 substituents, each independently halo, alkyl, cyano, aminocarbonyl or alkyloxy;

$Ar^2$ is naphthalenyl or phenyl, each optionally substituted with 1, 2 or 3 substituents, each independently halo, nitro, amino, mono- or di(alkyl)amino, cyano, alkyl, hydroxy, alkyloxy, carboxyl, alkyloxycarbonyl, aminocarbonyl or mono- or di(alkyl)aminocarbonyl;

$Ar^3$ is naphthalenyl or phenyl, optionally substituted with 1, 2 or 3 substituents, each independently alkyloxy, alkylcarbonylamino, methanesulfonyl, $Ar^1$carbonyloxyalkyl, $Ar^1$alkyloxycarbonyl, $Ar^1$alkyloxyalkyl, alkyl, halo, hydroxy, pyridinyl, morpholinyl, pyrrolyl, pyrrolidinyl, imidazo[1,2-a]pyridinyl, morpholinylcarbonyl, pyrrolidinylcarbonyl, amino or cyano;

$Het^2$ is a monocyclic heterocyclic radical that is pyrrolidinyl, dihydro-2H-pyranyl, pyranyl, dioxolyl, imidazolidinyl, tetrahydropyridinyl, tetrahydropyrimidinyl, pyrazolidinyl, piperidinyl, morpholinyl, dithianyl, thiomorpholinyl, piperazinyl, imidazolidinyl, tetrahydrofuranyl, 2H-pyrrolyl, pyrrolinyl, imidazolinyl, pyrazolinyl, pyrrolyl, imidazolyl, pyrazolyl, triazolyl, furanyl, thienyl, oxazolyl, dioxazolyl, oxazolidinyl, isoxazolyl, thiazolyl, thiadiazolyl, isothiazolyl, pyridinyl, 1H-pyridinyl, pyrimidinyl, pyrazinyl, pyridazinyl, triazinyl or tetrazolyl; or a bicyclic heterocyclic radical that is 2,3-dihydro-benzo[1,4]dioxine, octahydro-benzo[1,4]dioxine, octabicycloheptyl, benzopiperidinyl, quinolinyl, quinoxalinyl, indolyl, isoindolyl, chromanyl, benzimidazolyl, imidazo[1,2-a]pyridinyl, benzoxazolyl, benzodioxolyl, benzisoxazolyl, benzoxadiazolyl, benzothiazolyl, benzisothiazolyl, benzofuranyl, dihydroisobenzofuranyl, or benzothienyl; wherein each mono-, or bicyclic heterocyclic radical is optionally substituted on any atom with at least one radical that is $Ar^1$, $Ar^1$alkyl, $Ar^1$alkyloxyalkyl, halo, hydroxy, alkyl, piperidinyl, pyrrolyl, thienyl, oxo, alkyloxy, alkylcarbonyl, $Ar^1$carbonyl, mono- or di(alkyl)aminoalkyl, alkyloxyalkyl or alkyloxycarbonyl;

alkyl is a straight or branched saturated hydrocarbon radical having from 1 to 6 carbon atoms or a cyclic saturated hydrocarbon radical having from 3 to 6 carbon atoms; each hydrocarbon radical optionally substituted on at least one carbon atom with at least one radical that is phenyl, halo, trihalomethyl, aminocarbonyl, methyl, ethyl, propyl, isopropyl, t-butyl, cyano, oxo, hydroxy, formyl or amino; and alkenyl is a straight or branched unsaturated hydrocarbon radical having from 1 to 6 carbon atoms and having at least one unsaturated bond; or a cyclic unsaturated hydrocarbon radical having from 3 to 6 carbon atoms and having at least one-unsaturated bond; each hydrocarbon radical optionally substituted on at least one carbon atom with at least one radical that is phenyl, halo, cyano, oxo, hydroxy, formyl or amino.

15. The process according to claim 14, wherein the Alk-Y-Alk-L-moiety in the compounds of Formulas (IIa), (Ia) and (Ib) is benzyl and the Alk-L-moiety in the compound of Formula (III) is benzyl.

16. The process according to claim 14, further comprising converting the compound of Formula (Ia) or (Ib) into a therapeutically active, non-toxic acid addition salt by treatment with an acid.

17. The process according to claim 16, further comprising converting the acid addition salt into a free base by treatment with alkali.

18. The process according to claim 17, further comprising converting the free base into a stereochemically isomeric form, a N-oxide, or a quaternary ammonium salt.

19. The process according to claim 14, further comprising converting the compound of Formula (Ia) or (Ib) into a therapeutically active, non-toxic base addition salt by treatment with a base.

20. The process according to claim 19, further comprising converting the base addition salt into a free acid by treatment with an acid.

21. The process according to claim 20, further comprising converting the free acid into a stereochemically isomeric form, a N-oxide, or a quaternary ammonium salt.

22. The process according to claim 14, further comprising converting the compound of Formula (Ia) into the compound of Formula (Ib) or converting the compound of Formula (Ib) into the compound of Formula (Ia).

* * * * *

UNITED STATES PATENT AND TRADEMARK OFFICE
CERTIFICATE OF CORRECTION

| | | |
|---|---|---|
| PATENT NO. | : 8,138,334 B2 | Page 1 of 1 |
| APPLICATION NO. | : 11/913890 | |
| DATED | : March 20, 2012 | |
| INVENTOR(S) | : Frans Eduard Jenssens et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 284 days.

Signed and Sealed this
First Day of January, 2013

David J. Kappos
*Director of the United States Patent and Trademark Office*